United States Patent [19]
Shibata et al.

[11] Patent Number: 6,139,561
[45] Date of Patent: Oct. 31, 2000

[54] ULTRASONIC MEDICAL INSTRUMENT

[75] Inventors: Norikiyo Shibata, Yamato; Makoto Miyawaki, Tanashi; Mitsumasa Okada, Hachioji, all of Japan

[73] Assignee: Olympus Optical Co., Ltd., Tokyo, Japan

[21] Appl. No.: 09/250,087

[22] Filed: Feb. 16, 1999

[30] Foreign Application Priority Data

Apr. 16, 1998 [JP] Japan .................................. 10-106244
Dec. 14, 1998 [JP] Japan .................................. 10-354539

[51] Int. Cl.$^7$ ...................................................... A61B 17/32
[52] U.S. Cl. ............................................ 606/169; 606/207
[58] Field of Search ................................... 606/169, 170, 606/171, 205, 207; 604/22

[56] References Cited

U.S. PATENT DOCUMENTS 5,322,055 6/1994 Davison et al. .
5,873,873 2/1999 Smith et al. ............................. 606/170
5,906,628 5/1999 Miyawaki et al. ...................... 606/169

FOREIGN PATENT DOCUMENTS 8-505801 6/1996 Japan .
2592487 12/1996 Japan .

Primary Examiner—Michael Buiz
Assistant Examiner—Kevin Truong
Attorney, Agent, or Firm—Frishauf, Holtz, Goodman, Langer & Chick, P.C.

[57] ABSTRACT

A hand-piece comprises an arm main body which moves relative to a grip section, and an arm section having a clamp member openable and closable with respect to a probe section. As a result of movement of the arm main body relative to the grip section, the clamp member is shifted between a closure position in which the clamp member cooperates with the probe section to hold living tissue between the clamp member and the probe section, and an open position in which the clamp member is separated from the probe section to release the living tissue.

14 Claims, 14 Drawing Sheets

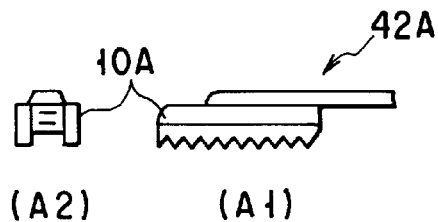
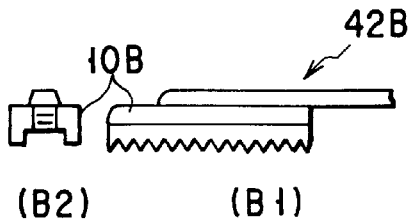
FIG. 9A  FIG. 9B
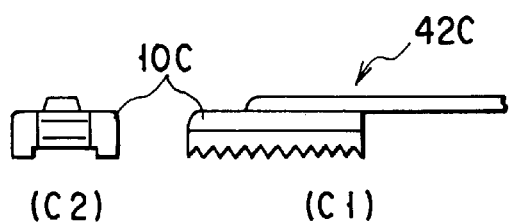
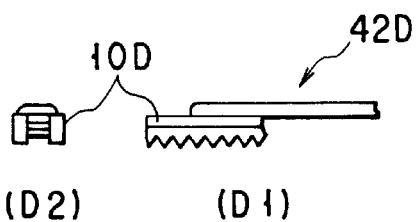
FIG. 9C  FIG. 9D
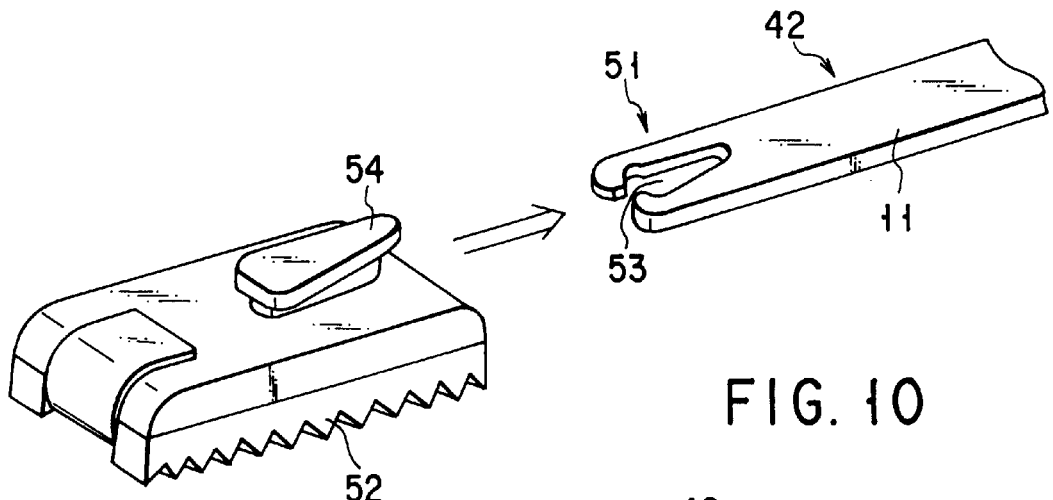
FIG. 10
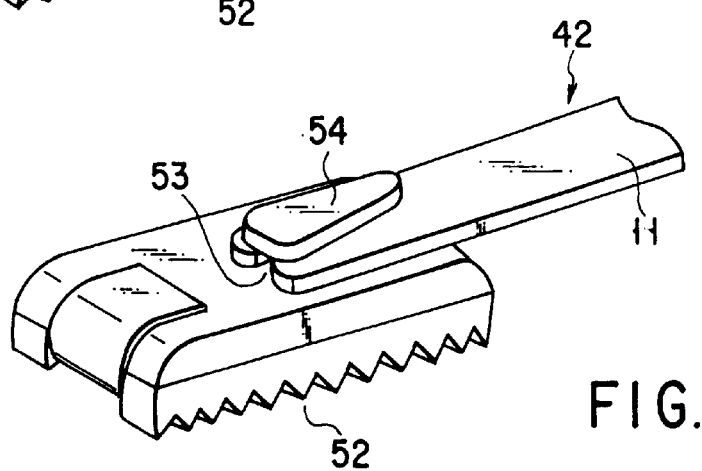
FIG. 11

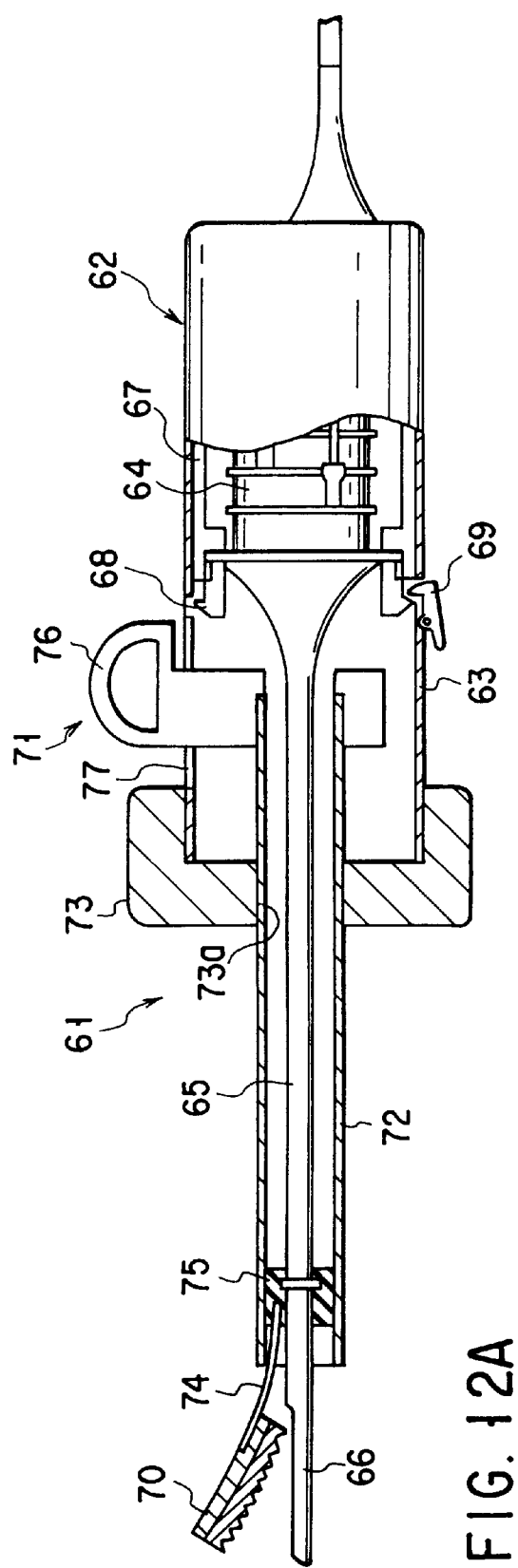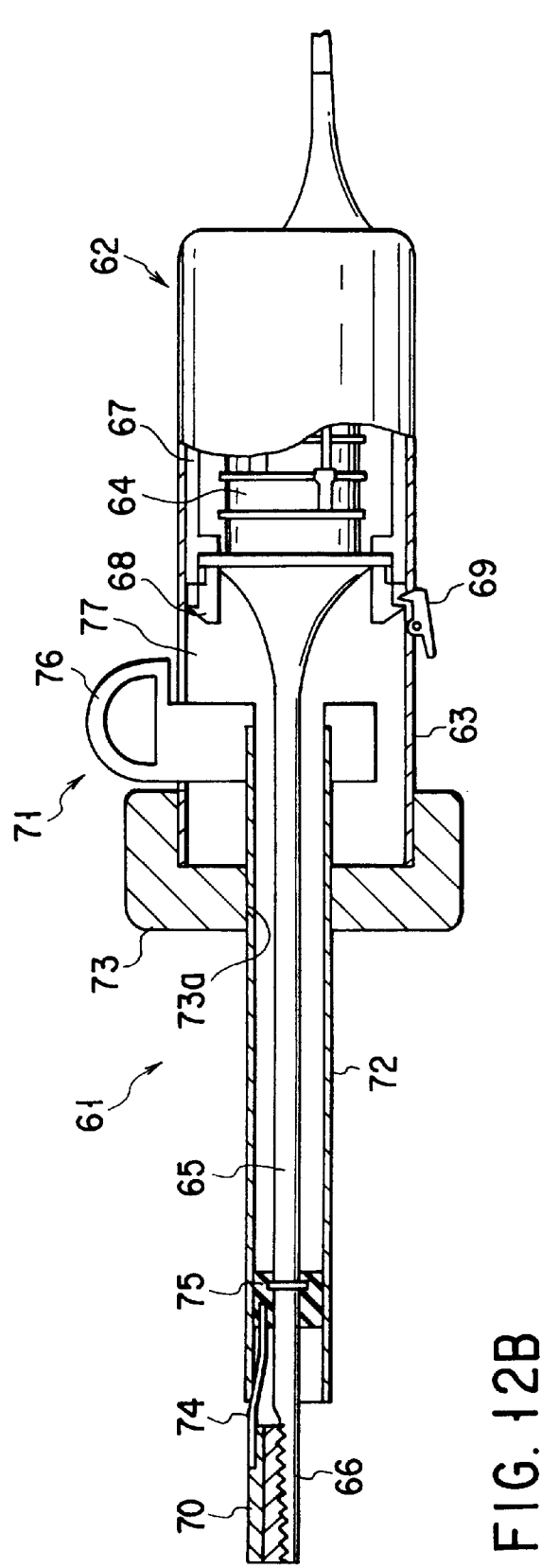
FIG. 12A
FIG. 12B

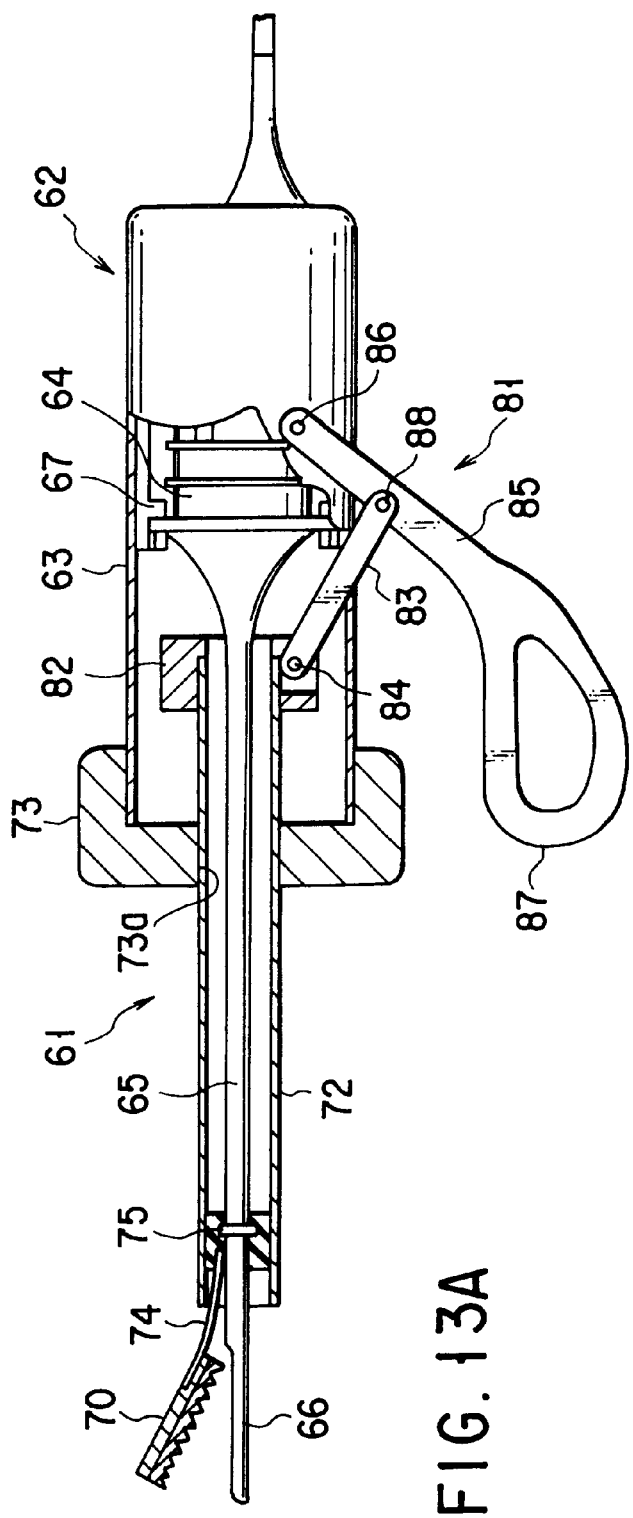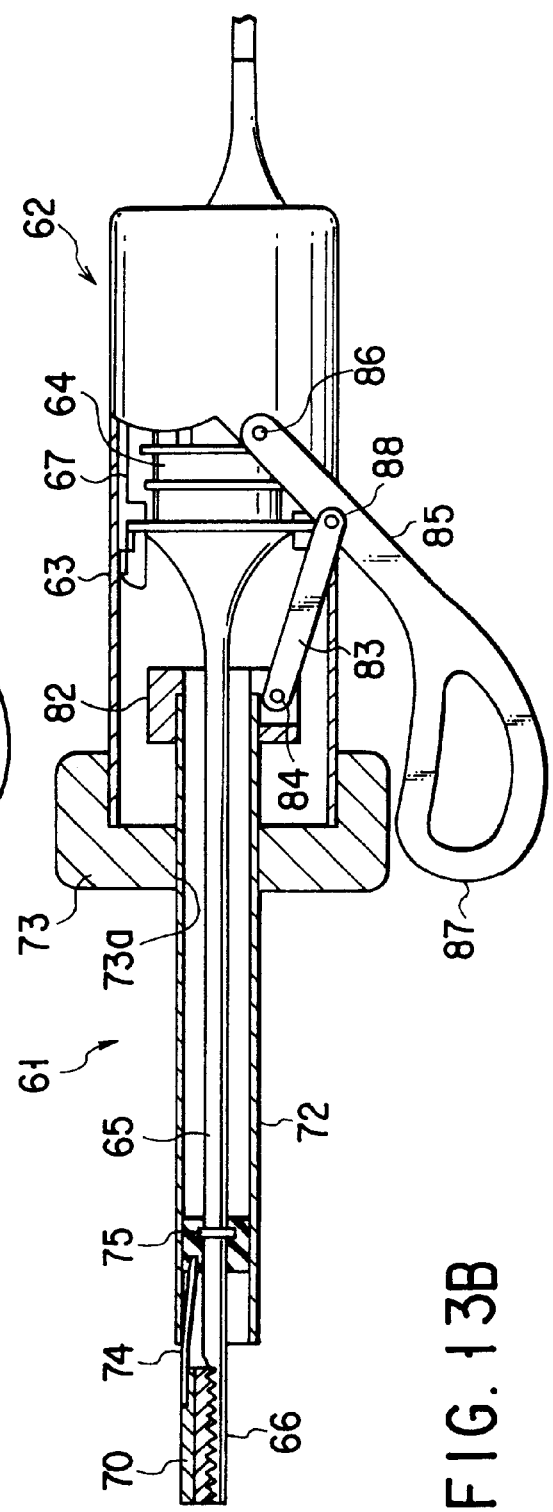

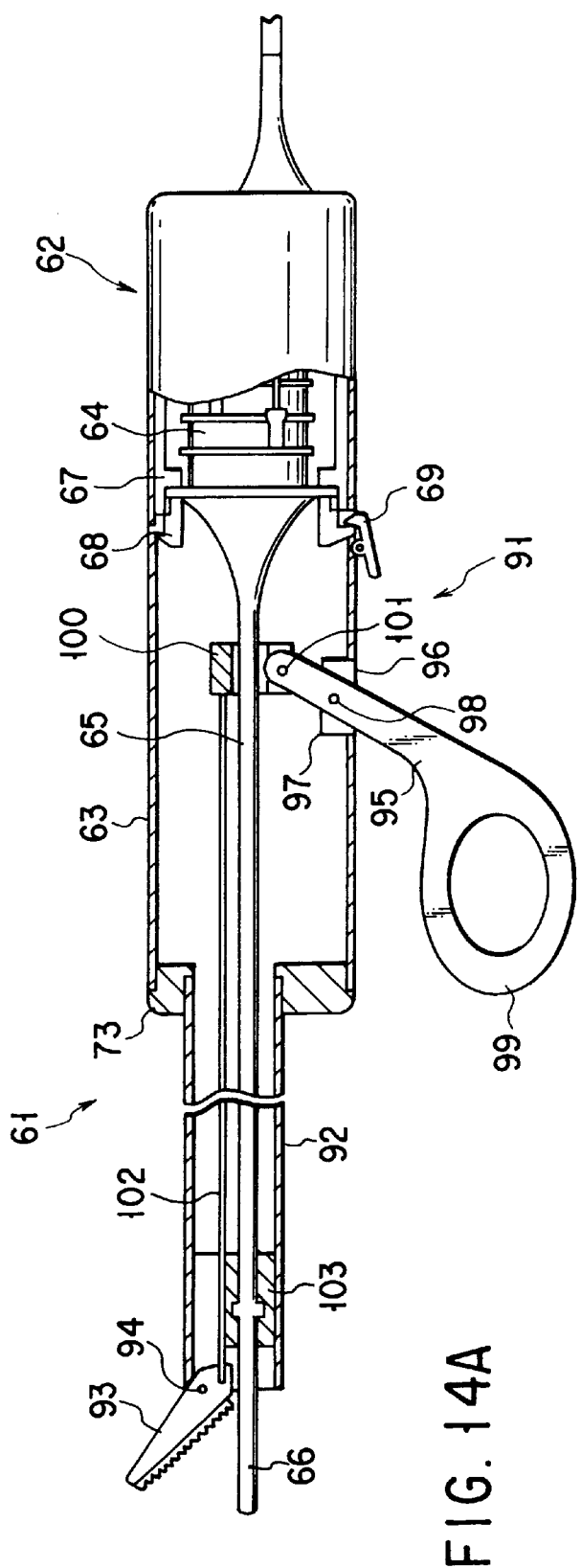
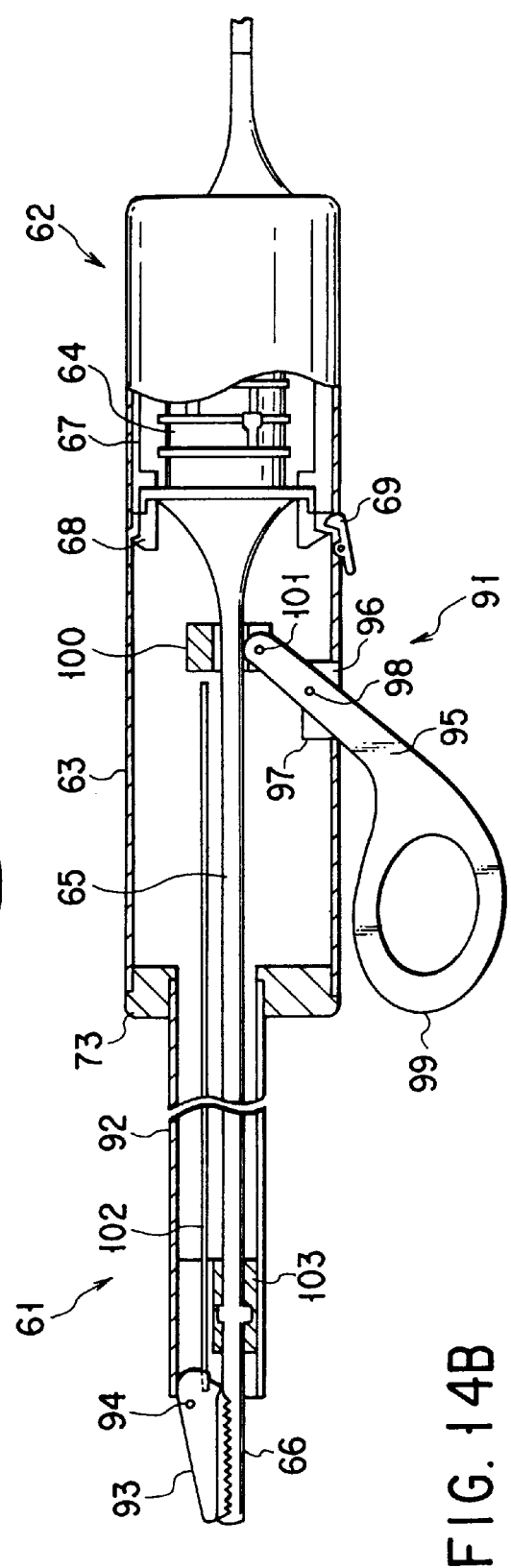

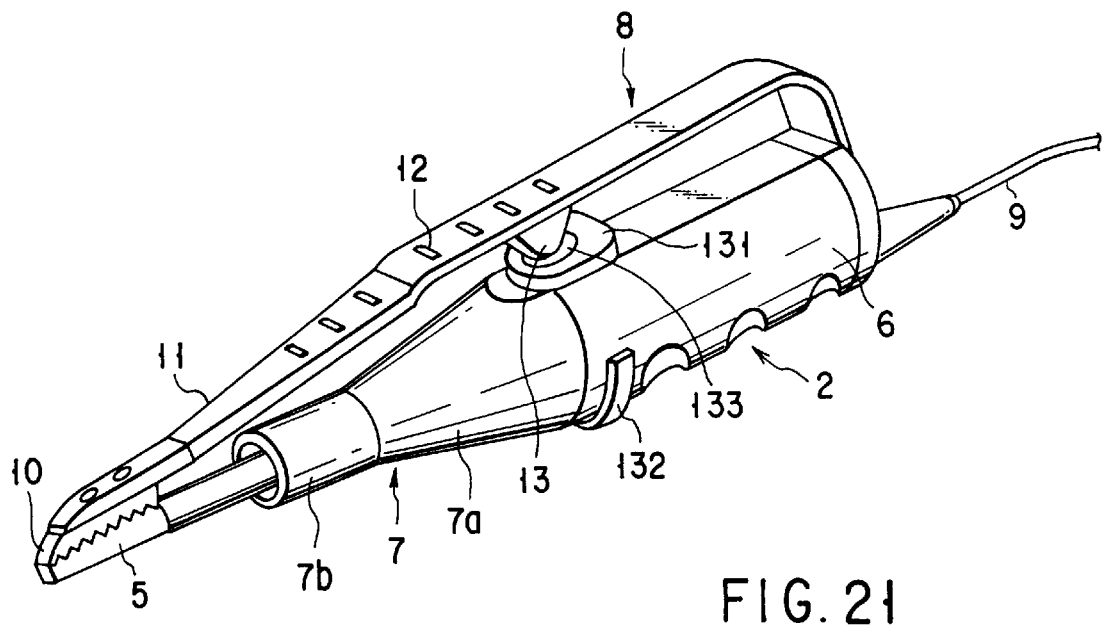
FIG. 21
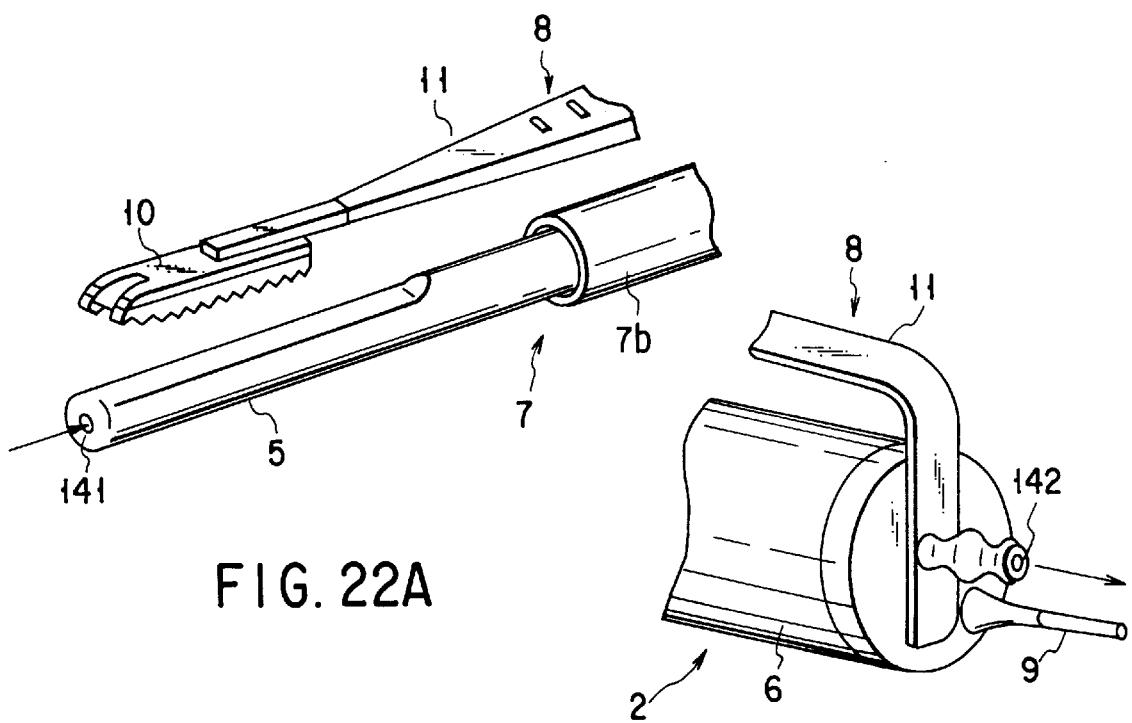
FIG. 22A
FIG. 22B

ULTRASONIC MEDICAL INSTRUMENT

BACKGROUND OF THE INVENTION

This invention relates to an ultrasonic medical instrument to be used when a surgical operation such as an abdominal operation is performed.

For example, U.S. Pat. No. 5,322,055, PCT National Publication No. 8-505801 (WO94/16631), and Japanese Patent No. 2592487 disclose ultrasonic coagulating/incising apparatuses as ultrasonic medical instruments each for use in combination with an endoscope to perform a surgical operation under the endoscope. In each of these apparatuses, a treatment section for ultrasonic coagulation and incision is provided at the distal end of a long and slender insertion section of the apparatus. Further, an operation handle section is provided at the proximal end of the insertion section. This handle section is used to operate the treatment section for ultrasonic coagulation and incision.

Since the insertion section of those ultrasonic coagulating/incising apparatuses is rather long, the position of the handle section is relatively remote from the affected part of the patient's body when the treatment section at the distal end of the insertion section is brought into contact with the affected part. At this time, the handle-gripping hand of the operator such as a doctor is liable to become unstable, and hence the handle section becomes hard to operate.

Although there are ultrasonic coagulating/incising apparatuses for abdominal operations which employ relatively short insertion sections, the conventional handle sections are shaped like guns as shown in U.S. Pat. No. 5,322,055, PCT National Publication No. 8-505801, etc. and hence not suitable for delicate treatments. Thus, the conventional handle sections have low operability.

BRIEF SUMMARY OF THE INVENTION

The invention has been developed in light of the above-described circumstances, and is aimed at providing an ultrasonic medical treatment which is suitable for abdominal operations and can be used in a reliable manner, thereby enhancing the performance of the operations.

To attain the aim, there is provided an ultrasonic medical instrument for transmitting ultrasonic oscillation to living tissue to thereby perform an ultrasonic treatment of the living tissue, comprising:

an instrument main body which includes an oscillator for generating ultrasonic oscillation, an oscillator cover covering the oscillator, a transmission section for amplifying and transmitting the ultrasonic oscillation from the oscillator, and a probe section provided at a distal end of the transmission section and being able to be brought into contact with the living tissue to transmit to the living tissue the oscillation from the transmission section; and operation means including an operation section which moves relative to the instrument main body, and a clamp member openable/closable with respect to the probe section, the operation means shifting the clamp member, as a result of the operations of the operation section relative to the instrument main body, between a closure position in which the clamp member cooperates with the probe section to hold the living tissue between the clamp member and the probe section, and an open position in which the clamp member is separated from the probe section to release the living tissue.

During performing an ultrasonic treatment, ultrasonic oscillation generated from the oscillator is amplified by the transmission section and then transmitted therefrom to the probe section located at the distal end of the instrument. At this time, the probe section is brought into contact with living tissue thereby to transmit the oscillation to it. As a result of relative movement of the oscillator cover and the operation section of the operation means, the clamp member is shifted between the closure position in which the clamp member cooperates with the probe section to hold the living tissue between the clamp member and the probe section, and the open position in which the clamp member is separated from the probe section to release the living tissue.

As described above, in the ultrasonic medical instrument of the invention, the oscillator cover is moved relative to the operation section of the operation means equipped with the clamp member openable/closable with respect to the probe section, thereby shifting the clamp member between the closure position in which the clamp member cooperates with the probe section to hold the living tissue between the clamp member and the probe section, and the open position in which the clamp member is separated from the probe section to release the living tissue. Accordingly, the medical instrument of the invention is suitable for abdominal operations and can realize operations of high performance.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 9A is a view, useful in explaining a standard coupling unit which is exchangeable with a detachable clamp section incorporated in the hand-piece of the ultrasonic medical instrument of the fourth embodiment;

FIG. 9B is a view, useful in explaining an oblong coupling unit which is exchangeable with the detachable clamp section incorporated in the hand-piece of the ultrasonic medical instrument of the fourth embodiment;

FIG. 9C is a view, useful in explaining a wide coupling unit which is exchangeable with the detachable clamp section incorporated in the hand-piece of the ultrasonic medical instrument of the fourth embodiment;

FIG. 9D is a view, useful in explaining a small coupling unit which is exchangeable with the detachable clamp section incorporated in the hand-piece of the ultrasonic medical instrument of the fourth embodiment;

FIG. 10 is a perspective view showing a modification of the grip section of the hand-piece included in the ultrasonic medical instrument of the fourth embodiment;

FIG. 11 is a perspective view showing a coupled state of the hand-piece and the grip section of FIG. 10;

FIG. 12A is a longitudinal sectional view showing a state in which a clamp section of a hand-piece incorporated in an ultrasonic medical instrument according to a fifth embodiment is open;

FIG. 12B is a longitudinal sectional view showing a state in which the clamp section employed in the fifth embodiment is closed;

FIG. 13A is a longitudinal sectional view showing a state in which a clamp section of a hand-piece incorporated in an ultrasonic medical instrument according to a sixth embodiment is open;

FIG. 13B is a longitudinal sectional view showing a state in which the clamp section employed in the sixth embodiment is closed;

FIG. 14A is a longitudinal sectional view showing a state in which a clamp section of a hand-piece incorporated in an ultrasonic medical instrument according to a seventh embodiment is open;

FIG. 14B is a longitudinal sectional view showing a state in which the clamp section employed in the seventh embodiment is closed;

FIG. 21 is a perspective view showing the ON-state of a switch section incorporated in the hand-piece of the tenth embodiment;

FIG. 22A is a perspective view illustrating a distal-end-side suction port in a hand-piece incorporated in an ultrasonic medical instrument according to an eleventh embodiment;

FIG. 22B is a perspective view illustrating a proximal-end-side suction port formed in the hand-piece of the ultrasonic medical instrument of the eleventh embodiment;

DETAILED DESCRIPTION OF THE INVENTION

Figure 1A:
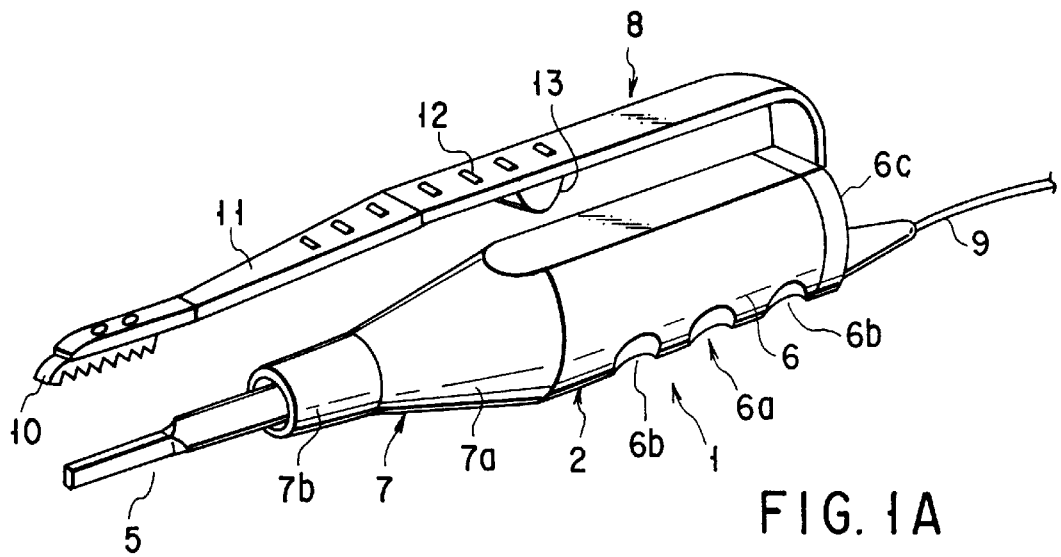
FIG. 1A is a perspective view showing a hand-piece incorporated in an ultrasonic medical instrument according to a first embodiment of the invention.
Figure 1B:
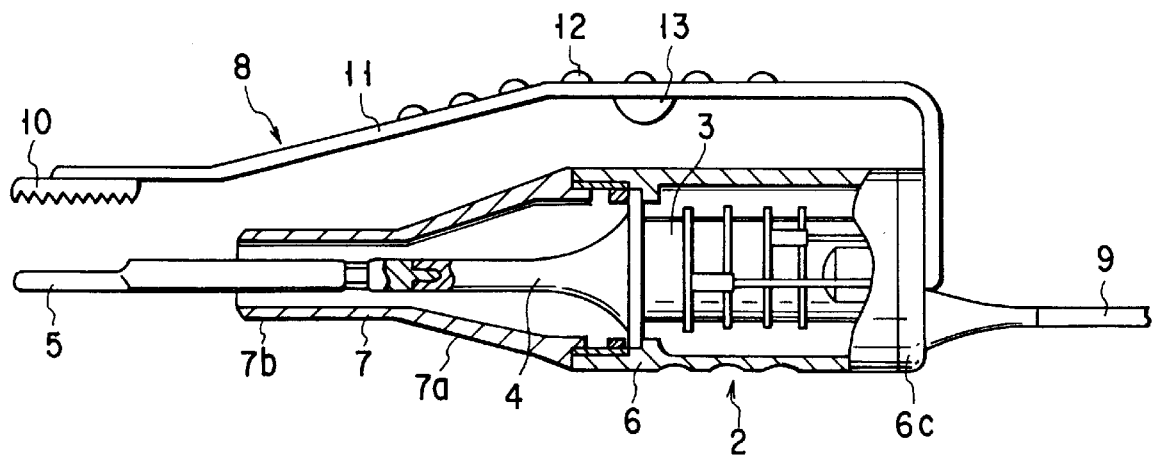
FIG. 1B is a longitudinal sectional view showing the hand-piece of the ultrasonic medical instrument according to the first embodiment.
Figure 1C:
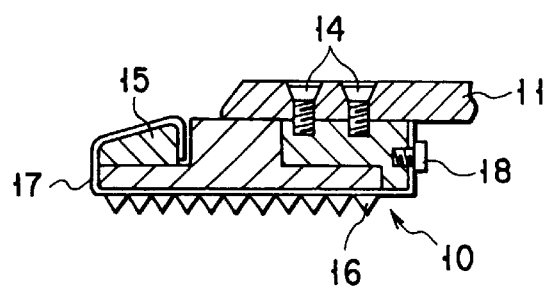
FIG. 1C is a longitudinal sectional view showing a clamp section incorporated in the ultrasonic medical instrument according to the first embodiment.

Referring first to FIGS. 1A–1C, a first embodiment of the invention will be described. FIG. 1A shows a hand-piece 1 incorporated in an ultrasonic coagulating/incising apparatus as an ultrasonic medical instrument, according to the first embodiment, used for surgical operations such as abdominal operations. The hand-piece 1 has a grip section (ultrasonic medical instrument main body) 2.

As is shown in FIG. 1B, an oscillator 3 is provided in the grip section 2 for generating ultrasonic oscillation. The oscillator 3 is connected to the proximal end of a horn (transmission section) 4. The distal end of the horn 4 is connected to the proximal end of a probe section 5. The ultrasonic oscillation of the oscillator 3 is amplified by the horn 4 and then transmitted to the probe section 5.

The grip section 2 further comprises a substantially cylindrical oscillator cover 6 which covers the oscillator 31 and a substantially conical casing 7 which covers the probe section 5. The casing 7 has a conical horn cover section 7a and a substantially cylindrical small-diameter section 7b connected to the distal end of the horn cover section 7a. The proximal end of the horn cover section 7a is connected to a distal end opening of the oscillator cover 6. The distal end of the probe section 5 is fixedly protruded forward through the distal end opening of the small-diameter section 7b of the casing 7.

A first finger groove section 6a is provided at the outer peripheral surface of the oscillator cover 6. This section 6a includes, for example, a plurality of finger grooves 6b formed parallel to each other in the outer peripheral surface of the cover 6.

A closure plate 6c is provided at the proximal end of the oscillator cover 6 and closes the rear opening of the cover. The proximal end of a substantially L-shaped arm section (operation means) 8 is secured to the closure plate 6c. The closure plate 6c is also connected to an end of a connection cord 9. The other end of the cord 9 is connected to the main body of an ultrasonic coagulating/incising apparatus (not shown).

The arm section 8 includes a clamp member 10 opposed to the distal end of the probe section 5 with a space interposed therebetween, and an arm main body (operation section) 11 extending from the proximal end of the clamp member 10. Non-slip ribs 12 are provided on the surface of the arm main body 11. A stopper 13 is protruded inward from the inner surface of the arm main body 11. The clamp member 10 is made to approach or separate from the distal end of the probe section 5, i.e. made to be open and closed, in accordance with relative operation between the first finger groove section 6a of the grip section 2 and the arm main body 11 of the arm section 8. More specifically, the clamp member 10 is movable between a closed position in which it cooperates with the probe section 5 to hold living tissue therebetween, and an open position, as shown in FIGS. 1A and 1B, in which it is separate from the probe section 5 to release the living tissue.

The clamp member 10 has a jaw 15 secured to the distal end of the arm main body 11 by securing screws 14, as is shown in FIG. 1C. A catching section 16 made of teflon (a trademark of Du Pont) is fitted in the jaw 15. The catching section 16 is coated with a plate 17 which has its proximal end fixed to the jaw 15 by a fixing screw 18.

The operation of the above-described structure will be described. When using the ultrasonic coagulating/incising apparatus of the embodiment, living tissue is placed between the probe section 5 as the distal end section of the hand-piece 1 and the clamp member 10. Subsequently, the arm main body 11 of the arm section 8, the oscillator cover 6 and the casing 7 are gripped, thereby causing the clamp member 10 as the distal end section of the arm main body 11 to approach the probe section 5 and hold the living tissue therebetween.

In this state, a foot switch (not shown) connected to the main body of the ultrasonic coagulating/incising apparatus is stepped, thereby supplying the oscillator 3 with a high frequency current from the main body of the apparatus through the cord 9. At this time, ultrasonic oscillation is generated from the oscillator 3 then amplified by the horn 4 and transmitted to the probe section 5. The ultrasonic oscillation of the probe section 5 causes frictional heat on the living tissue held between the probe section 5 and the clamp member 10, with the result that the living tissue is coagulated and incised.

The above structure provides advantages described below. In the hand-piece 1 of the ultrasonic coagulating/incising apparatus, the handle section of the hand-piece 1, which includes the arm main body 11 of the arm section 8, the oscillator cover 6 and the casing 7, can situate living tissue in a position close to the probe section 5 and the clamp member 10 which are used to actually catch it. Accordingly, when using the hand-piece 1 of the ultrasonic coagulating/incising apparatus of this embodiment, the operator such as a doctor can treat the affected part of the Patient's body in a position close to themselves. As a result, the hand-piece 1 gripped by the operator or doctor is free from vibration, which means that the hand-piece 1 is highly operable. In other words, the hand-piece 1 gripped by the operator is more stabilized during surgical operation than in the conventional case where a long and slender insertion section is interposed between the section used to actually treat living tissue and the handle section gripped and operated by the operator. This being so, the performance of abdominal operations can be enhanced.

Also, since the handle section of the hand-piece 1, which includes the arm main body 11 of the arm section 8, the oscillator cover 6 and the casing 7, is substantially V-shaped and similar in shape to a pincette, the operator can easily switch from ripping the handle section to gripping another surgical instrument.

Furthermore, since the distance is short between the treatment section ranging from the probe section 5 to the clamp member 10, and the operation section of the hand-piece 1 ranging from the arm main body 11 of the arm section 8 to the first finger groove section 6a of the oscillator cover 6, delicate operations can be performed easily. Accordingly, a small and fine affected part can be treated efficiently.

Figure 2:
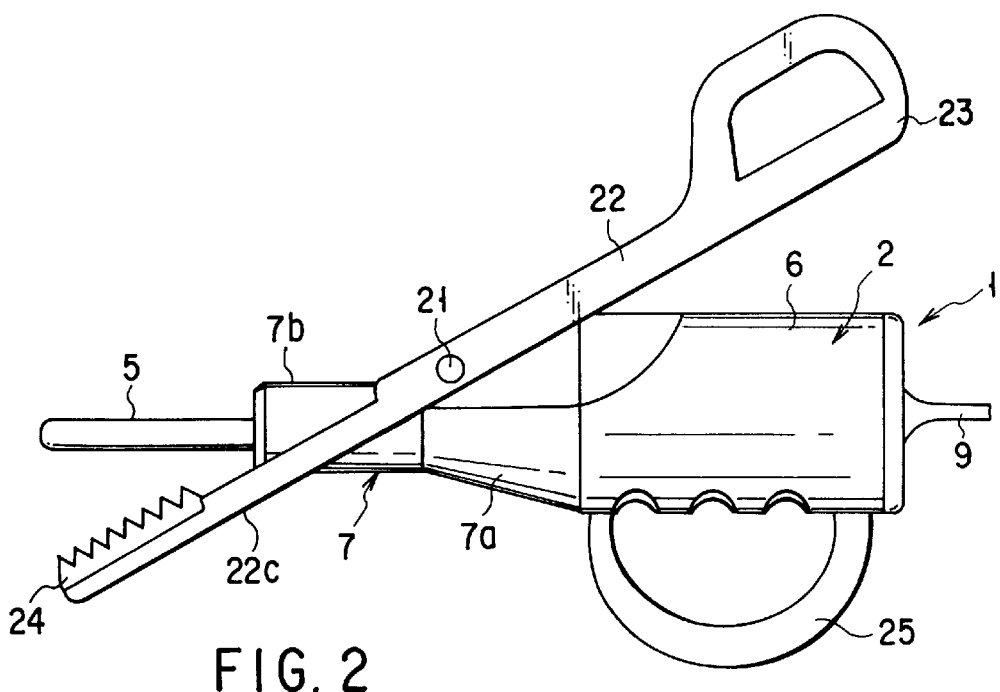
FIG. 2 is a side view showing a hand-piece incorporated in an ultrasonic medical instrument according to a second embodiment of the invention.
Figure 3:
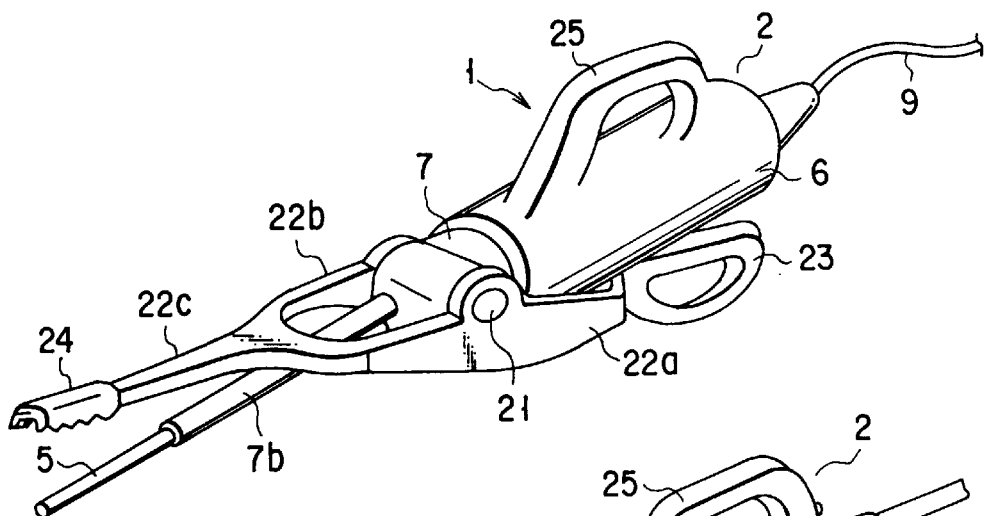
FIG. 3 is a perspective view showing the hand-piece incorporated in the ultrasonic medical instrument according to the second embodiment.

Referring then to FIGS. 2 and 3, a second embodiment of the invention will be described. This embodiment is obtained by changing the hand-piece 1 of the first embodiment (shown in FIGS. 1A–1C) as described below.

In the second embodiment, a rotatable pin 21 is provided on the outer surface of the casing 7 of the hand-piece 1, and a substantially Y-shaped arm section 22 is provided such that it can rotate about the pin 21. As a result, the arm section 22 has, at its proximal end, a substantially V-shaped, forked portion which consists of two branches 22a and 22b, as is shown in FIG. 3. The casing 7 of the hand-piece 1 is inserted between the two branches 22a and 22b.

Further, a ringhandle 23 is provided at the proximal end of the arm section 22. A single substantially linear clamp support arm 22c is provided at the distal-end-side of the arm section 22 such that it extends between the branches 22a and 22b. A clamp member 24 of the same structure as the clamp member 10 employed in the first embodiment is provided on the clamp support arm 22c.

A ringhandle 25 is provided on the outer surface of the oscillator cover 6. The fingers of the operator are inserted into the ringhandle 25 of the cover 6 and the ringhandle 23 of the arm section 22. By operating the inserted fingers, the treatment section between the probe section 5 and the clamp member 24 is opened and closed.

After that, the operation of the above structure will be described. When using the ultrasonic coagulating/incising apparatus of the second embodiment, first, the fingers of the operator are inserted into the ringhandle 25 of the oscillator cover 6 and the ringhandle 23 of the arm section 22, thereby separating the ringhandles 25 and 23 from each other to open the probe section 5 and the clamp member 24, which are provided at the distal-end-side of the hand-piece 1. In this state, living tissue is inserted between the probe section 5 and the clamp member 24.

Subsequently, the arm section 22 is gripped to make the ringhandles 23 and 25 to approach each other. At this time, the arm section 22 rotates about the rotatable pin 21 clockwise in FIG. 2. Accordingly, the clamp member 24 approaches the probe section 5, thereby holding the living tissue therebetween. The other operation is similar to that performed in the first embodiment.

Since the second embodiment employs the ringhandle 25 of the oscillator cover 6 and the ringhandle 25 of the arm section 22, it has the advantage, in addition to advantages as obtained in the first embodiment, that the probe section 5 and the clamp member 24 can be more easily opened than in the first embodiment. This is very useful, in particular, in peeling living tissue, since the instrument can be inserted between attached tissue pieces with the clamp member 24 and the probe section 5 closed, and then operated to open the clamp member 24 and probe section 5 in order to separate the tissue pieces.

In addition, since the clamp member 24 and the probe section 5 can be opened largely, relatively wide-range living tissue can be held therebetween. Accordingly, wide-range living tissue can be coagulated and incised at a time.

Figure 4:
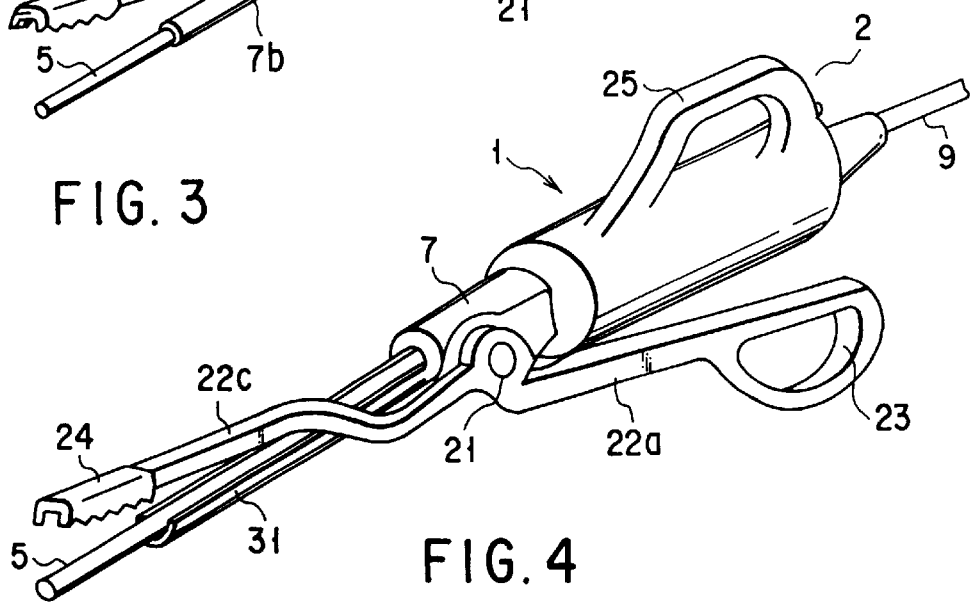
FIG. 4 is a perspective view showing a modification of the hand-piece incorporated in the ultrasonic medical instrument according to the second embodiment.

FIG. 4 shows a modification of the hand-piece 1 of the ultrasonic coagulating/incising apparatus according to the second embodiment (shown in FIGS. 2 and 3). This modification employs a probe cover 31 provided on an outer surface of the probe section 5 of the hand-piece 1 such that it protects the probe section 5 from being touched by the operator.

Figure 5:
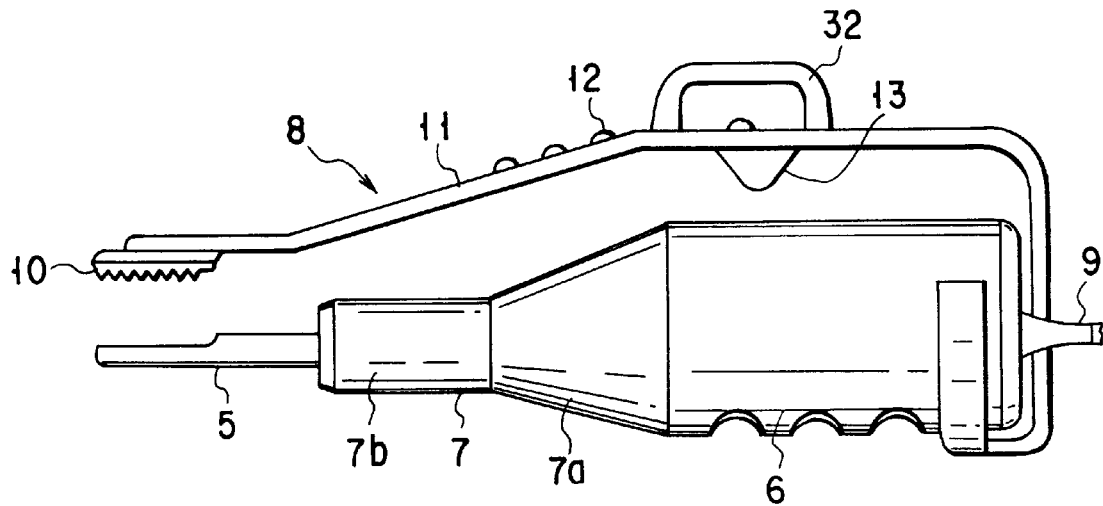
FIG. 5 is a side view showing a hand-piece incorporated in an ultrasonic medical instrument according to a third embodiment of the invention.

FIG. 5 illustrates a third embodiment of the invention. In this embodiment, a ringhandle 32 for peeling operation is provided on an outer surface of the arm main body 11 of the arm section 8 incorporated in the hand-piece 1 of the ultrasonic coagulating/incising apparatus of the first embodiment (shown in FIGS. 1A–1C).

Living tissue can be peeled by separating the arm main body 11 from the grip section 2 of the hand-piece 1, with the finger inserted in the ringhandle 32 of the arm main body 11. Therefore, the third embodiment has the advantage that it can easily peel living tissue, as well as similar advantages to those obtained in the first embodiment.

FIGS. 6A–9D show a fourth embodiment of the invention. This embodiment is obtained by changing the coupling section between the grip section 2 and the arm section 8 of the hand-piece 1 of the first embodiment (shown in FIGS. 1A–1C), as described below.

Figure 7:
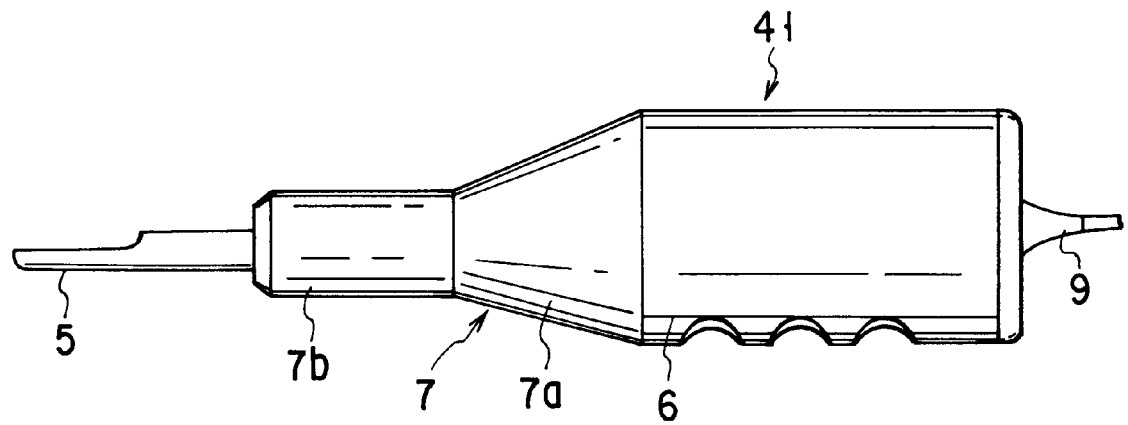
FIG. 7 is a side view showing a grip section employed in the hand-piece of the ultrasonic medical instrument of the fourth embodiment.
Figure 8A:
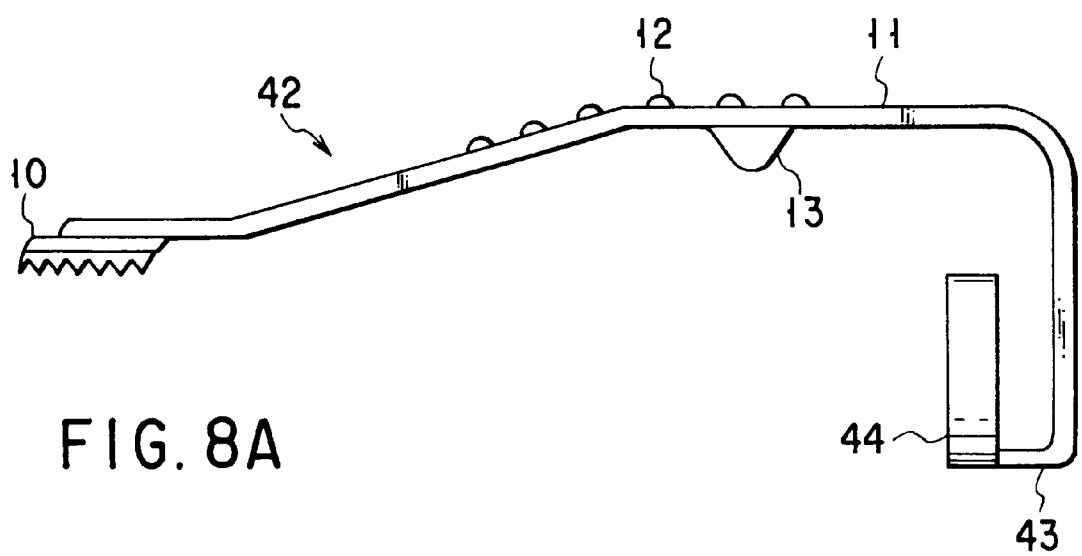
FIG. 8A is a side view showing a coupling operation section incorporated in the hand-piece of the ultrasonic medical instrument of the fourth embodiment.
Figure 8B:
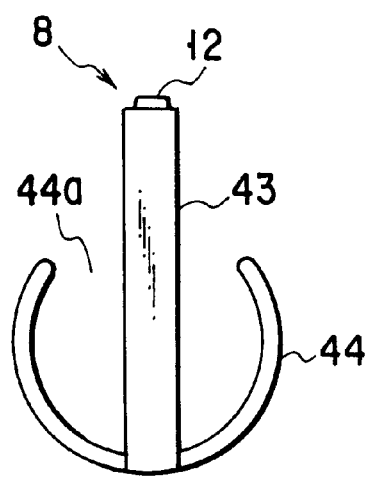
FIG. 8B is a back view illustrating the hand-piece of the ultrasonic medical instrument of the fourth embodiment.

As is shown in FIGS. 8A and 8B, this embodiment employs a coupling unit 42 obtained by separating the arm section 8 from the grip section 2 in the hand-piece 1 of the first embodiment, and shown in FIG. 7 a grip main body 41 constituted of the arm section 8 separated from the grip section 2.

The coupling unit 42 includes a substantially L-shaped bent section 43 formed at the rear end of the arm main body 11 as shown in FIG. 8A. The bent section 43 has a substantially C-shaped snap fit section 44 as shown in FIG. 8B.

Figure 6A:
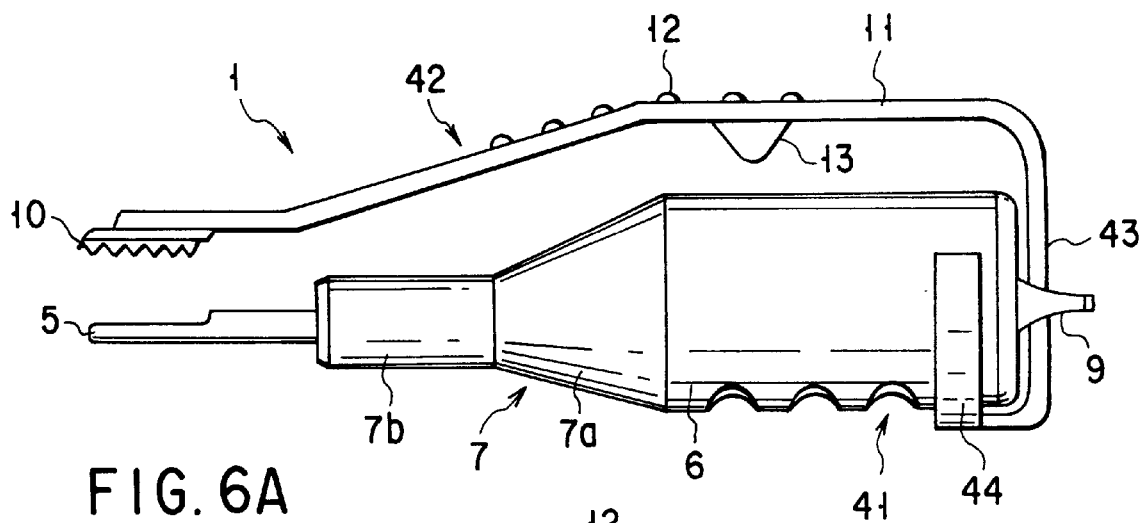
FIG. 6A is a side view showing a hand-piece incorporated in an ultrasonic medical instrument according to a fourth embodiment of the invention.
Figure 6B:
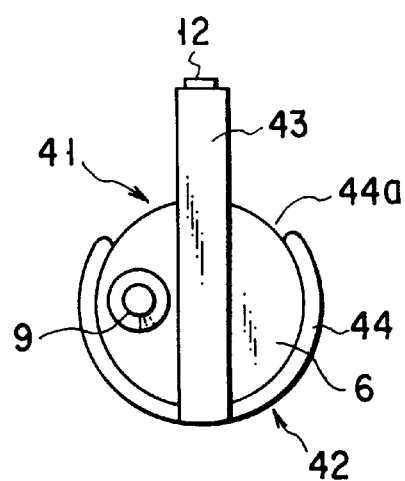
FIG. 6B is a back view illustrating the hand-piece of the ultrasonic medical instrument of the fourth embodiment.

The C-shaped portion of the snap fit section 44 has an inner diameter substantially equal to or slightly smaller than the outer diameter of the oscillator cover 6. Further, an open portion 44a of the snap fit section 44 has a smaller width than the outer diameter of the oscillator cover 6. The coupling unit 42 constructed as above is detachably attached to the rear end of the oscillator cover 6 of the grip main body 41, as is shown in FIGS. 6A and 6B.

Further, the fourth embodiment employs several types of coupling units and clamp members. For example, (A1) and (A2) of FIG. 9A show a standard coupling unit 42A with a standard clamp member 10A. Similarly, (B1) and (B2) of FIG. 9B show an oblong coupling unit 42B with an oblong clamp member 10B which has an axial length greater than the standard clamp member 10A. (C1) and (C2) of FIG. 9C show a wide coupling unit 42C with a wide clamp member 10C which has a width greater than the standard clamp member 10A. (D1) and (D2) of FIG. 9D show a small coupling unit 42D with a clamp member 10D smaller than the standard clamp member 10A.

The operation of the above-described structure will be described. After the hand-piece 1 of the fifth embodiment is used, the coupling unit 42 of the arm section 8 can be detached from the grip main body 41 using the detachable function of the snap fit section 44. In this state, the coupling unit 42 can be exchanged with the other types of coupling units 42, such as the standard one shown in (A1) and (A2) of FIG. 9A, the oblong one shown in (B1) and (B2) of FIG. 9B, the wide one shown in (C1) and (C2) of FIG. 9C and the small one shown in (D1) and (D2) of FIG. 9D.

Since as described above, in this embodiment, the hand-piece 1 can be used with an appropriately selected type of coupling unit 42, it can perform highly efficient medical treatments. Also, if the clamp member 10 is degraded, it can be easily exchanged with new one, together with the coupling unit 42. Thus, the fourth embodiment can provide an ultrasonic coagulating/incising apparatus of low cost.

FIGS. 10 and 11 illustrate a modification of the coupling unit 42 employed in the fourth embodiment (shown in FIGS. 6A–9D). In this modification, a clamp holding section 51 is provided at the distal end of the arm main body 11 for holding a detachable clamp member 52 which is obtained by separating the clamp member 10 from the arm main body 11 of the coupling unit 42 of the fourth embodiment.

As shown in FIG. 10, the clamp holding section 51 has a slit 53 formed in the distal end of the arm main body 11 of the coupling unit 42. On the other hand, the detachable clamp member 52 has a rib 54 projecting from the upper surface thereof so that it can be engaged with the slit 53 of the arm main body 11.

In this modification, the detachable clamp member 52 can be exchanged with another by disengaging the rib 54 from the slit 53 after using the hand-piece 1. Since the clamp member 52 can be detached from the coupling unit 42 and individually exchanged with another in this modification, an ultrasonic coagulating/incising apparatus can be provided at lower cost than in the case where hand-pieces equipped with different types of clamp members are prepared in accordance with different purposes.

Referring then to FIGS. 12A and 12B, a fifth embodiment of the invention will be described. FIG. 12A illustrates a hand-piece 61 incorporated in an ultrasonic coagulating/incising apparatus according to the fifth embodiment. The hand-piece 61 includes a grip section 62 which has a substantially cylindrical casing 63. An oscillator 64 is provided in the casing 63 at its proximal end side, and connected to the proximal end of a horn (transmission section) 65. The distal end of the horn 65 is connected to a probe section 66. Ultrasonic oscillation from the oscillator 64 is amplified by the horn 65 and then transmitted to the probe section 66.

A substantially cylindrical oscillator cover 67 which covers the oscillator 64 is provided at the proximal end side of the casing 63. An attachment 68 is attached to the distal end of the oscillator cover 67.

A stopper 69 is provided in the casing 63 such that it can be engaged with and disengaged from the attachment 68 of the oscillator cover 67. The attachment 68 and the stopper 69 permits the oscillator cover 67 to be attached to and detached from the casing 63.

The hand-piece 61 of the fifth embodiment further includes a clamp section 70 attached thereto such that it can be separated from and put into contact with the probe section 66, and an opening/closing mechanism 71 for opening and closing the clamp section 70 and the probe section 66. A movable sheath 72 extends from the mechanism 71 and covers the outer peripheral surface of the probe 66. The sheath 72 can slide along the axis of the probe section 66 through a guide port 73a formed in an axially center portion of a closure member 73 which closes the front opening of the casing 63.

An elastic member 74 in the form of a plate spring is provided such that its distal end is secured to the proximal end of the clamp section 70. The proximal end of the elastic member 74 is secured to an inner peripheral front-end portion of the movable sheath 72 by a fixing member 75. The elastic member 74 urges the clamp section 70 in a direction (in an opening direction) in which the section 70 is separated from the probe section 66.

A ringhandle 76 is secured to the proximal end of the movable sheath 72. A guide port 77 is formed in the outer peripheral surface of the casing 63 so that the ringhandle 76 can slide therethrough along the axis of the movable sheath 72. The ringhandle 76 is protruded from the sheath 72 to the outside of the sheath 72 through the guide port 77, and can move along the axis of the sheath 72.

The operation of the above structure will be described. When using the hand-piece 61 of the fifth embodiment, the operator's finger is inserted into the ringhandle 76 of the opening/closing mechanism 71, with the casing 63 gripped by the hand. In this state, the movable sheath 72 is moved axially, with the result that the clamp section 70 and the probe section 66 are opened or closed.

When the ringhandle 76 has reached the front end of the guide port 77 as shown in FIG. 12B, the elastic member 74 is pulled into the movable sheath 72 against its urging force. Since at this time, the clamp section 70 is urged by the distal end of the sheath 72 via the elastic member 74 in a direction in which the clamp section 70 and the probe section 66 are closed, living tissue is tightly held between the clamp section 70 and the probe section 66.

When the foot switch (not shown) has been stepped in that state, a high frequency current is supplied to the hand-piece 61 from the main body (not shown) of the ultrasonic coagulating/incising apparatus. The high frequency current is converted to ultrasonic oscillation by the oscillator 64, then amplified by the horn 65 and transmitted to the probe section 66. At this time, the living tissue held between the clamp section 70 and the probe section 66 is coagulated and incised due to friction caused by the oscillation between the tissue and the instrument.

After that, the ringhandle 76 is pulled to the operator side as shown in FIG. 12A, the clamp section 70 is moved by the urging force of the elastic member 74 in the opening direction in which it is separated from the probe section 66. Thus, the clamp section 70 and the probe section 66 are opened.

Since as described above, the clamp section 70 and the probe section 66 of the hand-piece 61 are opened and closed by the sliding operation of the ringhandle 76, the hand-piece 61 is free from excessive movement, which enables the operator to perform accurate opening/closing operations of the clamp section 70 and stable medical treatments, and also protects the operator from being greatly tired.

Referring to FIGS. 13A and 13B, a sixth embodiment of the invention will be described. This embodiment is obtained by changing the opening/closing mechanism 71 of the hand-piece 61 of the fifth embodiment (shown in FIGS. 12A and 12B) as described below.

In an opening/closing mechanism 81 employed in the sixth embodiment, a coupling member 82 is fixed to the proximal end of the movable sheath 72 of the fifth embodiment. The coupling member 82 is also coupled to one end of a link 83 so that the link 83 can rotate about a fulcrum 84.

One end of a movable handle 85 is coupled to the outer peripheral surface of the casing 63 of the hand-piece 61 so that it can rotate about a fulcrum 86. A ringhandle 87 is provided at the other end of the movable handle 85.

The other end of the link 83 is coupled to an middle portion of the movable handle 85 so that it can rotate about a fulcrum 88. The other structural elements are similar to those employed in the fifth embodiment.

The operation of the above structure will be described. When using the hand-piece 61 of this embodiment, the casing 63 of the hand-piece 61 is gripped with the fingers inserted in the ringhandle 87 of the movable handle 85. Subsequently, living tissue is held between the opened clamp section 70 and probe section 66, and then the movable handle 85 is gripped, thereby rotating the movable handle 85 about the fulcrum 86 clockwise in FIG. 13A. In accordance with the rotation of the movable handle 85, the coupling member 83 moves to the distal end side via the fulcrums 88 and 84, thereby pulling the elastic member 74 into the movable sheath 72 against the urging force of the member 74. As a result, the clamp section 70 is urged to the probe section 66 by the distal end of the movable sheath 72 via the elastic member 74, thereby tightly holding living tissue therebetween. The other structural elements are similar to those employed in the fifth embodiment.

Since in the sixth embodiment, the movable handle 85 is located in the vicinity of the center of gravity of the hand-piece 61, the hand-piece is well balanced. Accordingly, the user of the hand-piece 61 is protected from being greatly tired and therefore can perform an efficient medical treatment during an abdominal operation.

FIGS. 14A and 14B show a seventh embodiment of the invention. This embodiment is obtained by changing the opening/closing mechanism 71 of the hand-piece 61 of the fifth embodiment (shown in FIGS. 12A and 12B) as described below.

In an opening/closing mechanism 91 employed in the seventh embodiment, a stationary sheath 92 having its proximal end fixed to the closure member 73, which closes the front opening of the casing 63, is used in place of the movable sheath 72 of the fifth embodiment. The distal end of the stationary sheath 92 is connected to the proximal end of a clamp section 93 which is openable and closable with respect to the probe section 66, so that the clamp section 93 can pivot on a pivotal pin 94. A stationary member 103 may be provided, which secures the pivotal pin 94 of the clamp section 93 to the probe section 66.

An operation handle 95 for opening and closing the clamp section 93 is mounted on the casing 63 of this embodiment. More specifically, a handle mount hole 96 is formed in the outer peripheral surface of the casing 63, and a handle support section 97 is provided around the handle mount hole 96 such that it projects inward. The operation handle 95 is connected to the handle support section 97 so that it can pivot on a fulcrum 98. A ringhandle 99 extending to the outside of the casing 93 is provided at the free end of the operation handle 95.

A ring-shaped coupling member 100 is mounted in the casing 63 so that it can slide along the shaft of the horn 65. The proximal end of the operation handle 95 is coupled to the coupling member 100 within the casing 63 so that the handle 95 can pivot on a fulcrum 101.

A driving member 102 extending to the distal end side is secured, at its proximal end, to the coupling member 100. The distal end of the driving member 102 is rotatably coupled to the clamp section 93. The other structural elements are similar to those of the fifth embodiment.

The operation of the above structure will be described. When using the hand-piece 61 of this embodiment, the casing 63 of the hand-piece 61 is gripped with the fingers inserted in the ringhandle 99 of the operation handle 95. Subsequently, living tissue is held between the opened clamp section 93 and probe section 66, and then the movable handle 95 is gripped, thereby rotating the movable handle 95 about the fulcrum 98 clockwise in FIG. 14A. In accordance with the rotation of the operation handle 95, the coupling member 100 and the driving member 102 move rearward. Further, in accordance with the movement of the driving member 102, the clamp section 93 pivots on the pivotal pin 94 counterclockwise in FIG. 14A, thereby tightly holding living tissue between the clamp section 93 and the probe section 66 as understood from FIG. 14B. The other structural elements are similar to those employed in the fifth embodiment.

Since in the seventh embodiment, the operation handle 95 is located in the vicinity of the center of gravity of the hand-piece 61, the hand-piece is well balanced. Accordingly, the user of the hand-piece 61 is protected from being greatly tired and therefore can perform an efficient medical treatment during an abdominal operation.

Figure 15:
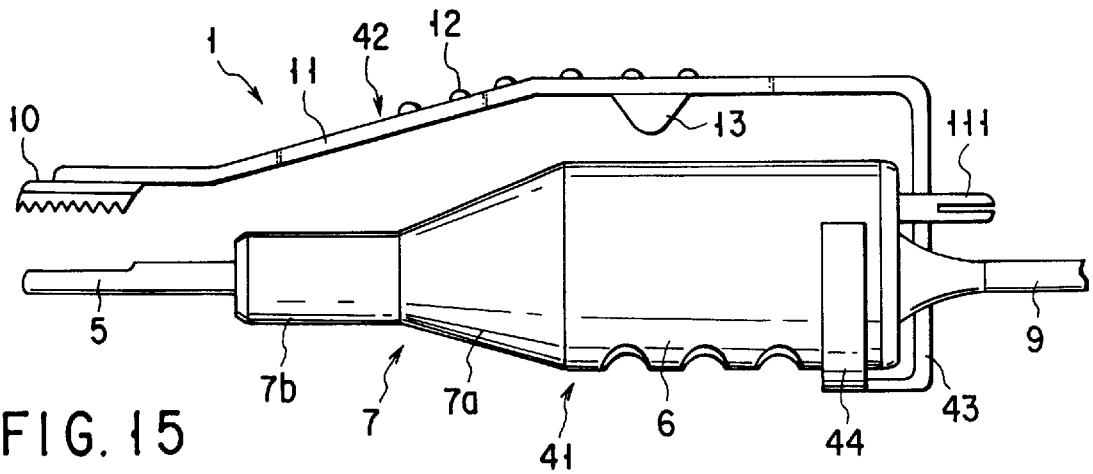
FIG. 15 is a side view showing a hand-piece incorporated in an ultrasonic medical instrument according to an eighth embodiment.
Figure 16:
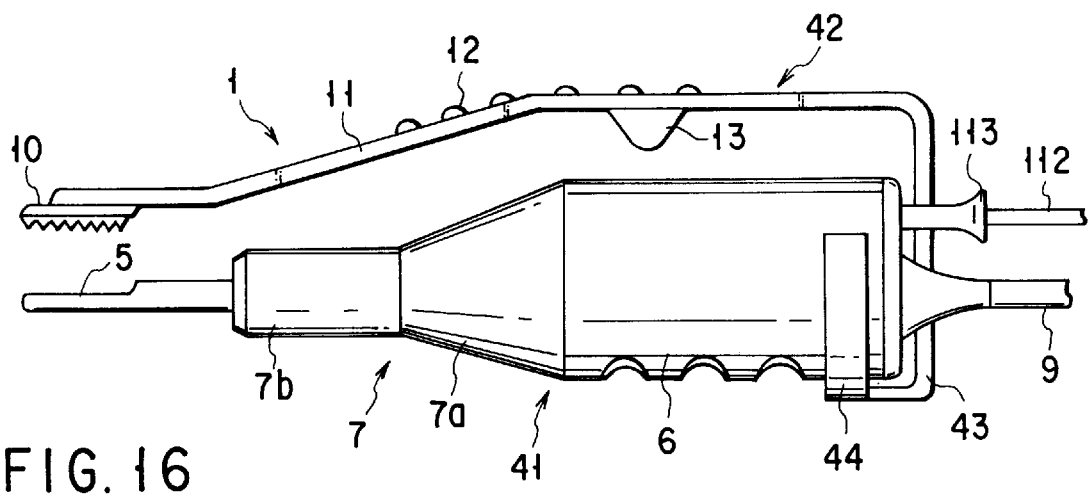
FIG. 16 is a side view illustrating a state in which a connection cord for supplying high frequency current is connected to a connection pin for high frequency current incorporated in the hand-piece in the eighth embodiment.
Figure 17:
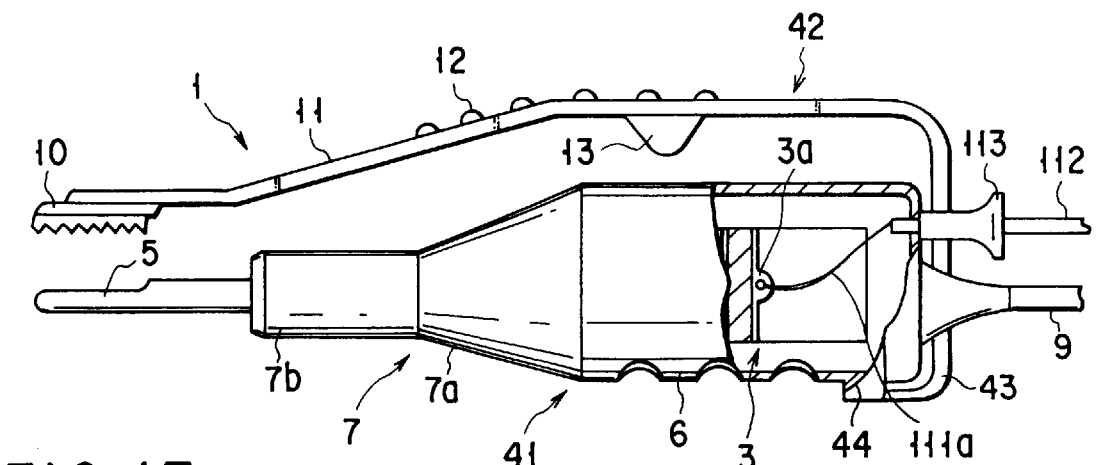
FIG. 17 is a side view, partly in section, illustrating an essential part of the hand-piece of the ultrasonic medical instrument of the eighth embodiment.

FIGS. 15–17 show an eighth embodiment of the invention. In this embodiment, the hand-piece 1 of the fourth embodiment (shown in FIGS. 6A–9D) is changed to a structure which also serves as a mono-polar type high frequency medical instrument as shown in FIG. 15.

Specifically, in the hand-piece 1 of the eighth embodiment, a connection pin 111 for high frequency current is protruded from the rear end of the oscillator cover 6, and disconnectably connected to the distal connector 113 of a connection cord 112 for supplying high frequency current as shown in FIG. 16.

The proximal end of the connection pin 111 is connected to one end of an internal cord 111*a* as shown in FIG. 17. The other end of the internal cord 111*a* is connected to an electrode 3*a* incorporated in the oscillator 3 in the oscillator cover 6. The electrode 3*a* is electrically connected to the probe section 5.

In the eighth embodiment, high frequency current can be supplied to the probe section 5 by connecting the connection pin 111 of the hand-piece 1 to the connector 113 of the connection cord 112 for supplying high frequency current. Accordingly, the medical instrument of this embodiment can perform both ultrasonic treatments and high frequency treatments using high frequency current. This means that this instrument has a high treatment capacity.

Figure 18:
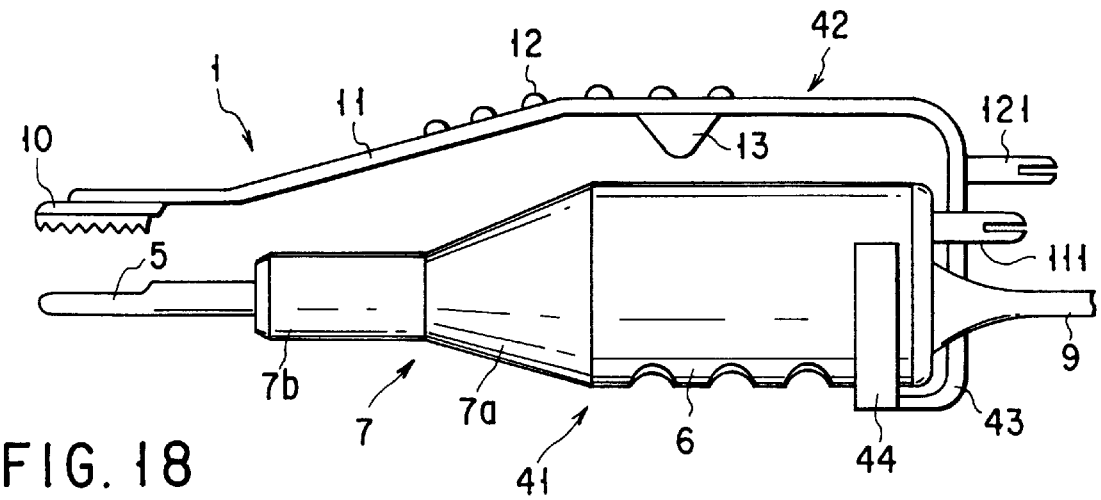
FIG. 18 is a side view showing a hand-piece of an ultrasonic medical instrument according to a ninth embodiment.
Figure 19:
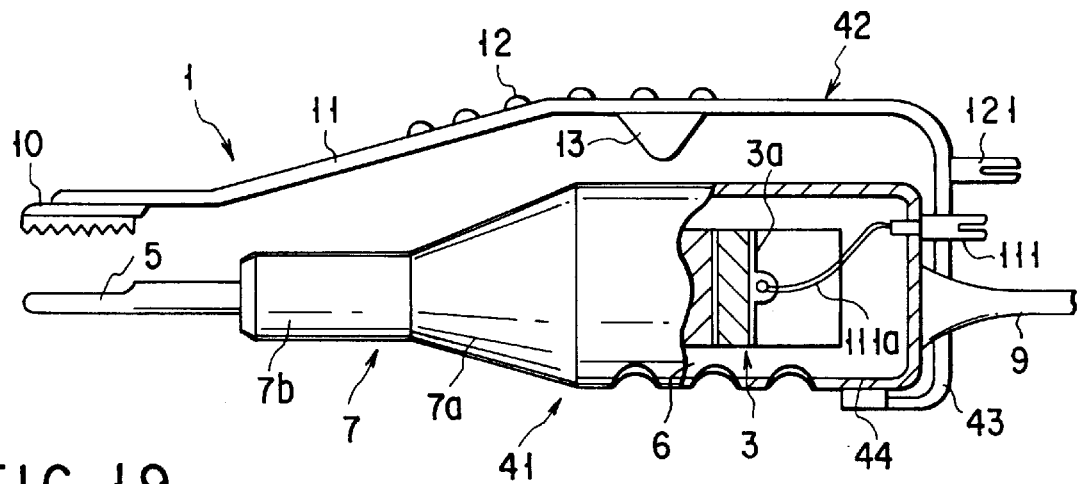
FIG. 19 is a side view, partly in section, illustrating an essential part of the hand-piece of the ultrasonic medical instrument of the ninth embodiment.

Referring now to FIGS. 18 and 19, a ninth embodiment of the invention will be described. In this embodiment, the hand-piece 1 of the eighth embodiment (shown in FIGS. 15–17) is changed to a structure which also serves as a bipolar type high frequency medical instrument.

Specifically, in the hand-piece 1 of the ninth embodiment, a second connection pin 121 for high frequency current is protruded from a bent section 43 of the arm main body 11, and disconnectably connected to the distal connector 113 of the connection cord 112 for supplying high frequency current (see FIG. 16).

In the ninth embodiment, high frequency current can be supplied to the probe section 5 and the clamp member 10 to enable bipolar treatments by connecting the connector 113 of the high frequency current supplying connection cord 112 to each of the connection pin 111 of the oscillator cover 6 and the second connection pine 121 of the bent section 43 of the arm main body 11. Accordingly, the medical instrument of this embodiment can perform both ultrasonic treatments and high frequency treatments using high frequency current. This means that this instrument has a high treatment capacity.

Figure 20:
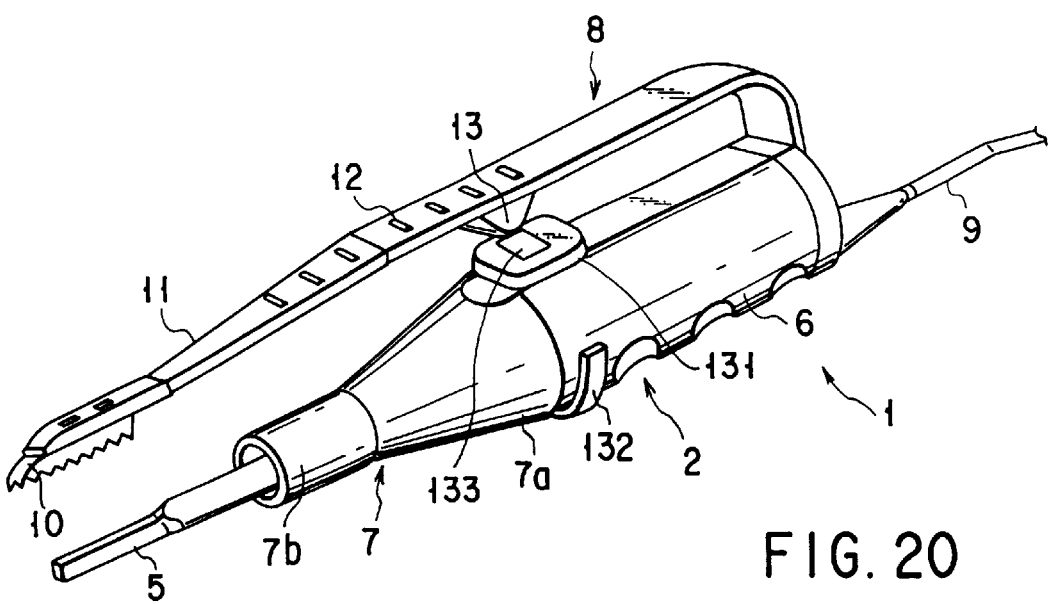
FIG. 20 is a side view showing a hand-piece of an ultrasonic medical instrument according to a tenth embodiment.

Referring then to FIGS. 20 and 21, a tenth embodiment of the invention will be described. In this embodiment, a hand switch 131 is detachably attached, using a snap fit 132, to the outer peripheral surface of the oscillator cover 6 of the hand-piece 1 of the first embodiment (shown in FIGS. 1A–1C). A switch section 133 is, for example, provided on the upper surface of the hand switch 131 for turning on and off the instrument which performs ultrasonic and high frequency treatments.

Further, a stopper 13 is provided on the inner surface of the arm main body 11 of the arm section 8 such that it is opposed to the switch section 133 with a space therebetween. The stopper 13 is configured so that it can be pressed against the switch section 133, as is illustrated in FIG. 19.

Accordingly, when the arm main body 11 of the arm section 8 is gripped, the switch section 133 is pushed, thereby turning on and off the instrument which performs ultrasonic and high frequency treatments. This means that the switch section 133 can be turned on and off without stepping the foot switch, and hence that treatments can be performed at a high efficiency and erroneous stepping of the foot switch can be prevented. Moreover, turn-on/off of the switch section 133 can be achieved by increasing/decreasing the impedance.

FIGS. 22A and 22B show an eleventh embodiment of the invention. In the eleventh embodiment, a suction conduit 141 is formed through center portions of the probe section 5, the horn 4, the oscillator 3 of the hand-piece 1 of the first embodiment (FIGS. 1A–1C), as is shown in FIG. 22A. A proximal side suction port 142 which communicates with the suction conduit 141 is provided in the proximal end of the hand-piece 1 as shown in FIG. 22B. The proximal side suction port 142 can be connected to a suction tube (not shown) connected to a suction device (not shown).

When in this embodiment, bleeding has suddenly occurred during treatment using the hand-piece 1, the region in which the operation is being performed can be kept clear by drawing the blood through the suction conduit 141. If necessary, a water supply tube can be used in place of the suction tube. The region of the operation can be cleaned by supplying water thereto through the water supply tube. Since thus, the region of the operation can be secured during ultrasonic treatment without any particular water supply/suction tube, the instrument can achieve highly efficient treatments.

Figure 23:
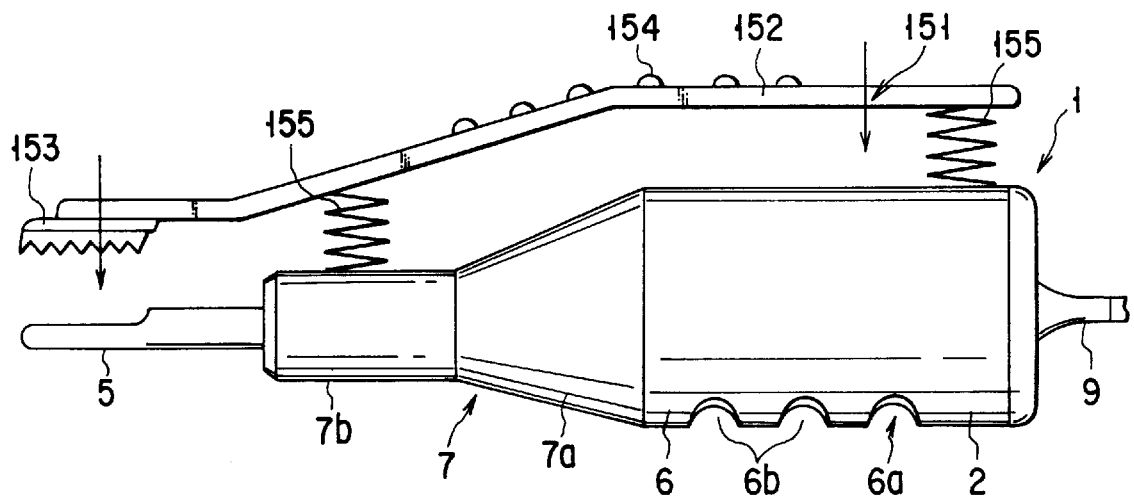
FIG. 23 is a side view showing a hand-piece employed in an ultrasonic medical instrument according to a twelfth embodiment.

FIG. 23 illustrates a twelfth embodiment of the invention. In this embodiment, the arm section 8 of the hand-piece 1 of the first embodiment (FIGS. 1A–1C) is changed as stated below.

The hand-piece 1 of the twelfth embodiment employs an arm member 151 which can move toward and away from the grip section 2 in a manner parallel thereto. The arm member 151 includes a substantially linear arm main body (second grip section) 152 and a clamp section 153 provided on the distal end of the arm main body 152. The clamp section 153 is opposed to the distal end of the probe section 5 with a space therebetween. Non-slip ribs 154 are provided on the arm main body 152.

Two spring members 155 are interposed in front and rear positions between the arm member 151 and the grip section 2, and urge the arm member 151 in a direction away from the grip section 2. In this state, the clamp section 153 is held in its open position in which it is separated from the probe section 5.

When the arm member 151 is made to approach the grip section 2 in a parallel manner against the urging force of the spring members 151, the clamp section 153 is moved toward its closure position in which it approaches the probe section 5.

When using the hand-piece 1 of this embodiment, the entire arm main body 152 of the arm member 151 is made to approach the grip section 2 in a parallel manner as indicated by the arrows in FIG. 23, by pushing a substantially center portion of the arm main body 152 toward the grip section 2. At this time, the clamp section 153 is moved, together with the arm body 152 of the arm member 151, toward its closure position in which it contacts the probe section 5, thereby enabling holding of living tissue between the clamp section 153 and the probe section 5.

When in this state, the foot switch (not shown) connected to the main body (not shown) of the ultrasonic coagulating/incising apparatus has been stepped, high frequency current is supplied to the oscillator 3 from the main body via the cord 9. At this time, ultrasonic oscillation is generated from the oscillator 3 then amplified by the horn 4 and transmitted to the probe section 5. The ultrasonic oscillation of the probe section 5 causes frictional heat on the living tissue held between the probe section 5 and the clamp section 153, with the result that the living tissue is coagulated and incised.

As described above, in the twelfth embodiment, the entire arm main body 152 of the arm member 151 is pushed against the urging force of the spring members 155, such that it approaches the grip section 2 in a parallel manner. As a result, the clamp section 153 is moved to its closure position in which living tissue can be held between itself and the probe section 5. Since the clamp section 153 is engaged with the probe section 5 parallel to each other, living tissue held therebetween can be cut uniformly.

Figure 24:
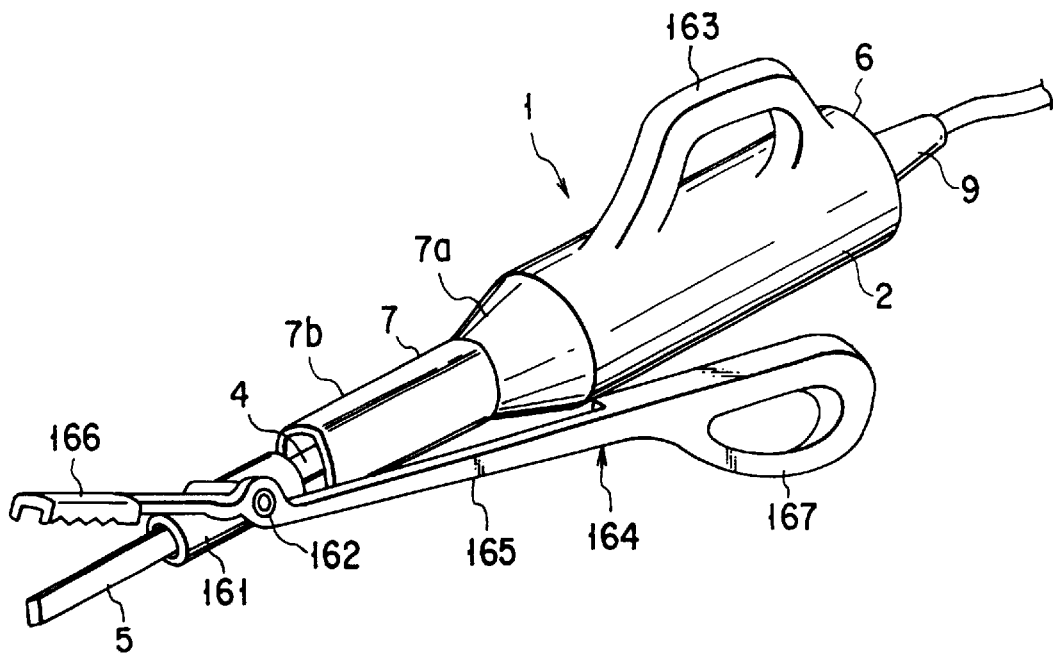
FIG. 24 is a perspective view showing a hand-piece employed in an ultrasonic medical instrument according to a thirteenth embodiment.

FIG. 24 illustrates a thirteenth embodiment of the invention. In this embodiment, the hand-piece 1 has a large-diameter stationary section 161 formed between the horn 4 and the probe section 5 integral with them as one body. The stationary section 161 has an arm shaft support (fulcrum) 162 located at a node (at which no ultrasonic oscillation occurs) of the ultrasonic oscillation transmission system through which ultrasonic oscillation supplied from the oscillator 3 and amplified by the horn 4 is transmitted to the probe section 5.

The hand-piece 1 of the thirteenth embodiment has a substantially elliptic first ring section (first ringhandle) 163 protruded from the outer surface of the oscillator cover 6 for inserting the fingers therein.

An arm member 164 is rotatably supported by the arm shaft support 162, and has a substantially linear arm main body 165. A clamp section 166 is provided at the distal end of the arm main body 165 such that it is opposed to the distal end of the probe section 5 with a space therebetween. A substantially elliptic second ring section (second ringhandle) 167 is provided at the proximal end side of the arm main body 165.

When using the hand-piece 1 of this embodiment, the first ring section 163 of the grip section 2 and the second ring section 167 of the arm member 164 are relatively opened and closed with the user's fingers inserted in the first and second ring sections 163 and 167. In accordance with the relative closing and opening operations of the first and second ring sections 163 and 167, the clamp section 166 approaches and separate from the probe section 5, respectively. In other words, the clamp section 166 and the probe section 5 are shifted between a closure position in which they contact each other and hold living tissue therebetween, and an open position in which they separate from each other and release living tissue therefrom.

Since as described above, the hand-piece 1 of the thirteenth embodiment employs the large-diameter stationary section 161 formed between the horn 4 and the probe section 5 integral therewith, and the arm shaft support 162 which rotatably supports the arm member 164 on the stationary section 161, the arm member 164 at the clamp section 166 side and the stationary section 161 at the probe section 5 side can be individually exchanged with new ones when they are worn at the arm shaft support 162 due to friction. This can decrease the maintenance cost, as compared with the case of repairing the entire hand-piece 1.

Figure 25:
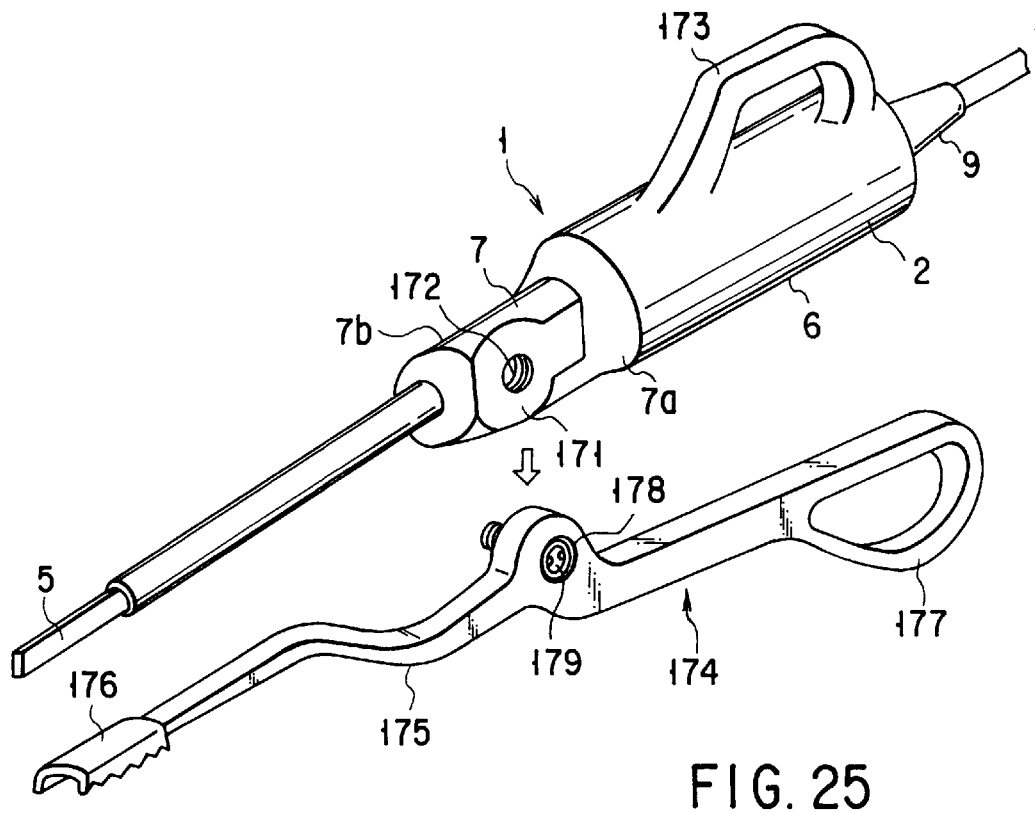
FIG. 25 is an exploded perspective view illustrating an essential part of an ultrasonic medical instrument according to a fourteenth embodiment.
Figure 26A:
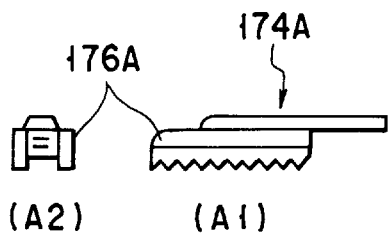
FIG. 26A is a view, useful in explaining a standard coupling unit which is exchangeable with an arm member employed in the hand-piece of the ultrasonic medical instrument of the fourteenth embodiment.
Figure 26B:
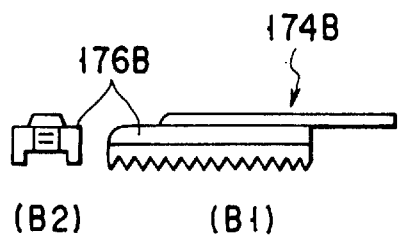
FIG. 26B is a view, useful in explaining an oblong coupling unit which is exchangeable with the arm member employed in the hand-piece of the ultrasonic medical instrument of the fourteenth embodiment.
Figure 26C:
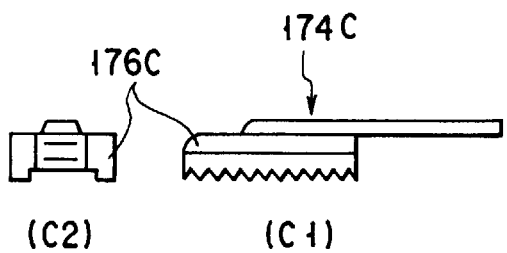
FIG. 26C is a view, useful in explaining a wide coupling unit which is exchangeable with the arm member employed in the hand-piece of the ultrasonic medical instrument of the fourteenth embodiment.
Figure 26D:
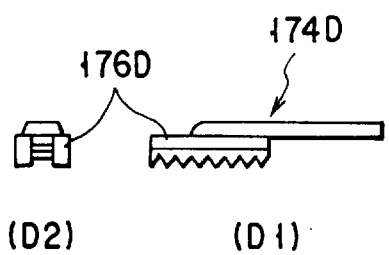
FIG. 26D is a view, useful in explaining a small coupling unit which is exchangeable with the arm member employed in the hand-piece of the ultrasonic medical instrument of the fourteenth embodiment.

Referring to FIGS. 25–26D, a fourteenth embodiment of the invention will be described. This embodiment employs an arm coupling section 171 at the horn 4. The arm coupling section 171 has a screw hole 172 formed therein. Further, a substantially elliptic first ring section (first ringhandle) 173 for inserting the fingers therein is protruded from the outer surface of the oscillator cover 6.

An arm member 174 can be connected to and disconnected from the arm coupling section 171. The arm member 174 has a substantially linear arm main body 175. A clamp section 176 is provided at the distal end of the arm main body 175 such that it is opposed to the distal end of the probe section 5 with a space therebetween. Also, a substantially elliptic second ring section (second ringhandle) 177 for inserting the fingers therein constitutes the proximal end of the arm main body 175.

A screw insertion hole 178 is formed in a longitudinally substantially center portion of the arm main body 175. The arm member 174 can be rotatably attached to the arm coupling section 171 by inserting a fixing screw 179 into the screw insertion hole 178 and the screw hole 172 of the arm coupling section 171.

Further, the fourteenth embodiment employs several types of arm members 174 with different clamp sections. For example, (A1) and (A2) of FIG. 26A show a standard arm member 174A with a standard clamp section 176A. Similarly, (B1) and (B2) of FIG. 26B show an oblong arm member 174B with an oblong clamp section 176B which has an axial length greater than the standard clamp section 176A. (C1) and (C2) of FIG. 26C show a wide arm member 174C with a wide clamp section 176C which has a width greater than the standard clamp section 176A. (D1) and (D2) of FIG. 26D show a small arm member 174D with a clamp section 176D smaller than the standard clamp section 176A.

The operation of the above-described structure will be described. Where the arm coupling section 171 and the arm member 174 are coupled to each other, the hand-piece 1 can be used as a scissors type ultrasonic medical instrument.

Also, after the hand-piece 1 is used, the arm member 174 can be detached from the arm coupling section 171 by removing the fixing screw 179 from the screw hole 172. The detached arm member 174 can be selectively exchanged with another type arm member which has another type clamp section, such as the standard type shown in (A1) and (A2) of FIG. 26A, the oblong type shown in (B1) and (B2) of FIG. 26B, the wide type shown in (C1) and (C2) of FIG. 26C and the small type shown in (D1) and (D2) of FIG. 26D.

Since as described above, in the hand-piece 1 of this embodiment, an appropriately selected type of arm member 174 can be attached to the arm coupling section 171, the hand-piece can perform highly efficient medical treatments. Also, if the clamp section 176 is degraded, it can be easily exchanged with new one, together with the arm member 174. Thus, the fourteenth embodiment can provide an ultrasonic coagulating/incising apparatus of low cost. In addition, the hand-piece 1 can be used as a knife type ultrasonic medical treatment, with the arm member 174 detached from the arm coupling section 171. Thus, the hand-piece 1 of this embodiment is very convenient in use.

Figure 27:
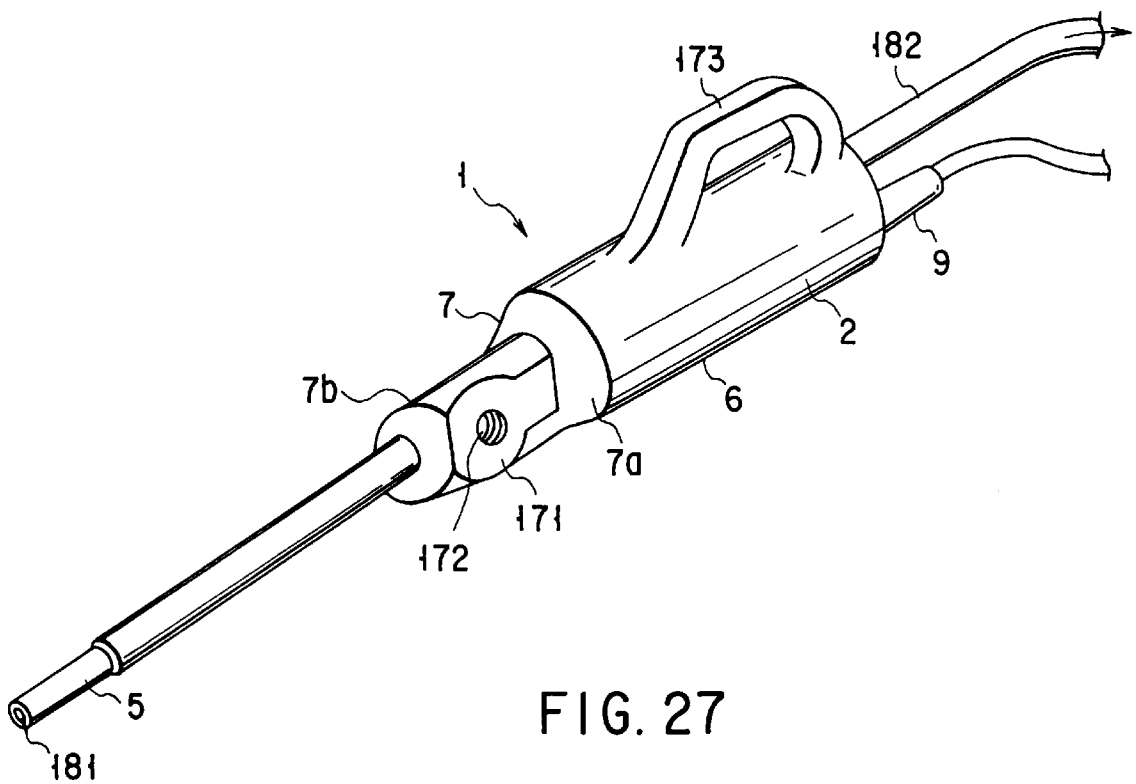
FIG. 27 is a perspective view illustrating a distal-end-side suction port in a hand-piece incorporated in an ultrasonic medical instrument according to a fifteenth embodiment.

Referring further to FIG. 27, a fifteenth embodiment of the invention will be described. This embodiment is obtained by changing the hand-piece 1 of the fourteenth embodiment (shown in FIGS. 25–26D) as described below.

In this embodiment, a suction conduit 181 is formed through is formed through center portions of the probe section 5, the horn 4, the oscillator 3 of the hand-piece 1 of the fourteenth embodiment. A proximal side suction port 142 (see FIG. 22B) which communicates with the suction conduit 181 is formed in the proximal end of the hand-piece 1. The proximal side suction port 142 can be connected to a suction tube 182 connected to a suction device (not shown).

Like the hand-piece 1 of the fourteenth embodiment, the hand-piece 1 of this embodiment can be used as a scissors type ultrasonic medical instrument, with the arm member 174 coupled to the arm coupling section 171 (see FIG. 25).

Also, the hand-piece 1 can be used as a knife type ultrasonic medical treatment, with the arm member 174 detached from the arm coupling section 171. If at this time, the suction device is driven, the instrument can be used as an ultrasonic suction instrument, which means that the hand-piece 1 of this embodiment is much more convenient in use.

Figure 28:
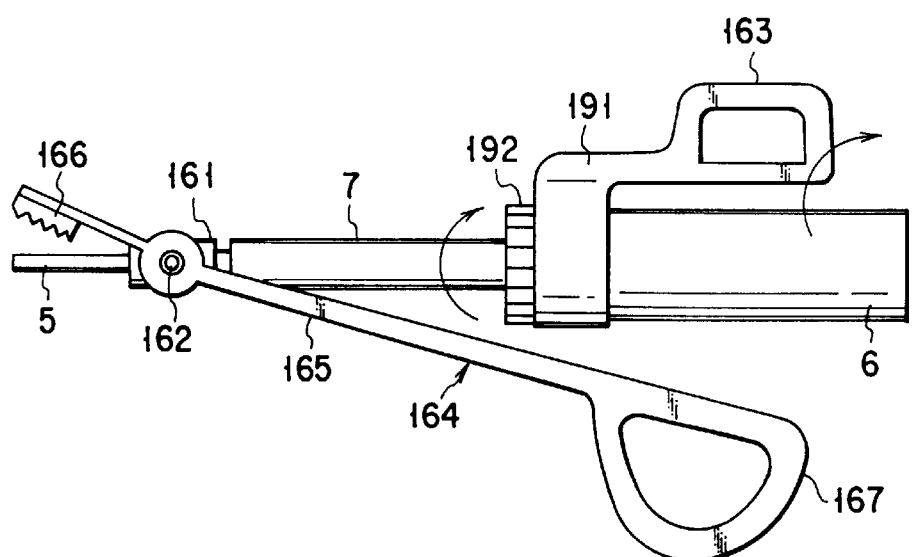
FIG. 28 is a side view showing the outward appearance of a hand-piece employed in an ultrasonic medical instrument according to a sixteenth embodiment.

FIG. 28 illustrates a sixteenth embodiment of the invention. In this embodiment, a rotary member 191, which includes the first ring section 163, is rotatably coupled to the outer surface of the oscillator cover 6 incorporated in the hand-piece 1 of the thirteenth embodiment (see FIG. 24). Further, a screw member 192 is screwed on the outer peripheral surface of the oscillator cover 6 in contact with the front end of the rotary member 191. When the screw member 192 is loosened, the rotary member 191 is supported on the outer peripheral surface of the oscillator cover 6 such that it can rotate about the axis of the cover 6. When, on the other hand, the screw member 192 is fastened, the rotary member 191 is fixed in a desired rotational position.

The above-described structure has an advantage as below. Since this embodiment employs the rotary member 191 rotatably coupled to the outer peripheral surface of the oscillator cover 6, and the first ring section 163 included in the member 191, the rotational position of the first ring section 163 can be easily adjusted with respect to the probe section 5. As a result, where the angular fixed position of the probe section 5 is not correctly set with respect to the angular fixed position of the horn-side oscillator cover 6 after the probe section 5 is connected, by screw-in connection, to the oscillator-side horn 4, angular positioning of the first ring section 163 and the probe section 5 can be performed by rotating the rotary member 191 on the outer peripheral surface of the oscillator cover 6 about the axis of it.

The invention is not limited to the above-described embodiments, but can be modified in various manners without departing from its gist.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic medical instrument which transmits ultrasonic oscillation to living tissue to thereby perform an ultrasonic treatment of the livings tissue, the ultrasonic medical instrument comprising:

an instrument main body including an oscillator which generates ultrasonic oscillation, an oscillator cover which covers the oscillator, a transmission section which amplifies and transmits the ultrasonic oscillation from the oscillator, and a probe section provided at a distal end of the transmission section which contacts the living tissue and transmits to the living tissue the ultrasonic oscillation from the transmission section; and operation means including an operation section extending from the oscillator cover toward the probe section along the instrument main body, and a clamp body provided at a distal end of the operation section and opposed to the probe section such that the clamp body is openable and closable with respect to the probe section, wherein the operation means shifts the clamp body, as a result of movement of the operation section relative to the instrument main body, between a closure position in which the clamp member cooperates with the probe section to hold the living tissue between the clamp body and the probe section, and an open position in which the clamp body is separated from the probe section to release the living tissue.

2. The ultrasonic medical instrument according to claim 1, wherein the operation section has an operation-section-side grip section which grips the operation section, and wherein the oscillator cover includes an instrument-main-body-side grid section which operates together with the operation section.

3. The ultrasonic medical instrument according to claim 1, wherein the operation section extends from a proximal end of the oscillator cover.

4. The ultrasonic medical instrument according to claim 1, wherein when the clamp body is opened and closed, the operation section and the clamp body of the operation means move in substantially the same direction.

5. The ultrasonic medical instrument according to claim 1, wherein the operation means is removably attached to the instrument main body.

6. The ultrasonic medical instrument according to claim 5, wherein the operation means further includes a plurality of exchangeable members attachable to the instrument main body, the exchangeable members having clamp members of different shapes which are used for different operations.

7. The ultrasonic medical instrument according to claim 1, wherein the clamp body is detachably attached to the operation section.

8. The ultrasonic medical instrument according to claim 7, wherein the clamp body includes a plurality of section-side grip section which grips the operation section, and wherein the oscillator cover includes an instrument-main-body-side grip section which operates together with the operation section.

9. An ultrasonic medical instrument which transmits ultrasonic oscillation to living tissue to thereby perform an ultrasonic treatment of the living tissue, comprising:

an instrument main body including an oscillator which generates ultrasonic oscillation, an oscillator cover which covers the oscillator, a transmission section which amplifies and transmits the ultrasonic oscillation from the oscillator, and a probe section provided at a distal end of the transmission section which contacts the living tissue to transmit to the living tissue the ultrasonic oscillation from the transmission section; and operation means including an operation section supported by a support shaft substantially perpendicular to a longitudinal axis of the instrument main body, and a clamp body provided at a distal end of the operation section and opposed to the probe section such that the clamp body is openable and closable with respect to the probe section, wherein the operation means shifts the clamp body, as a result of movement of the operation section relative to the instrument main body, between a closure position in which the clamp body cooperates with the probe section to hold the living tissue between the clamp body and the probe section, and an open position in which the clamp body is separated from the probe section to release the living tissue.

10. The ultrasonic medical instrument according to claim 9, wherein the operation section has an operation-section-side grip section for gripping the operation section, and wherein the oscillator cover includes an instrument-main-body-side grip section for operating together with the operation section.

11. The ultrasonic medical instrument according to claim 9, wherein the operation section is removably attached to the instrument main body.

12. The ultrasonic medical instrument according to claim 11, wherein the operation section includes a plurality of exchangeable members which are attachable to the instrument main body, and the exchangeable members have respective clamping portions of different shapes for different treatments.

13. The ultrasonic medical instrument according to claim 9, wherein the operation section is removably attached to the operation section.

14. The ultrasonic medical instrument according to claim 13, wherein the clamp body includes a plurality of exchangeable members attachable to the operation section, and the exchangeable members have respective clamping portions of different shapes for different treatments.

* * * * *